US007649084B2

(12) United States Patent
Ferguson

(10) Patent No.: US 7,649,084 B2
(45) Date of Patent: Jan. 19, 2010

(54) RECOMBINANT GLYCOPROTEINS RELATED TO FELINE THYROTROPIN

(75) Inventor: Duncan C. Ferguson, Bogart, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 33 days.

(21) Appl. No.: 10/579,090

(22) PCT Filed: Nov. 12, 2004

(86) PCT No.: PCT/US2004/037793

§ 371 (c)(1),
(2), (4) Date: Apr. 11, 2007

(87) PCT Pub. No.: WO2005/047319

PCT Pub. Date: May 26, 2005

(65) Prior Publication Data

US 2008/0139466 A1      Jun. 12, 2008

Related U.S. Application Data

(60) Provisional application No. 60/519,302, filed on Nov. 12, 2003, provisional application No. 60/534,205, filed on Jan. 5, 2004.

(51) Int. Cl.
*C07K 14/59* (2006.01)
*C07K 19/00* (2006.01)
*A61K 38/24* (2006.01)
*C12P 21/08* (2006.01)
*C07H 21/04* (2006.01)

(52) U.S. Cl. ............ 530/397; 514/8; 530/388.24; 536/23.4; 536/23.51

(58) Field of Classification Search ............ None
See application file for complete search history.

(56) References Cited

U.S. PATENT DOCUMENTS

| | | | |
|---|---|---|---|
| 4,036,945 | A | 7/1977 | Haber |
| 4,331,647 | A | 5/1982 | Goldenberg |
| 5,196,513 | A | 3/1993 | Ryan et al. |
| 5,560,922 | A | 10/1996 | Chien et al. |
| 5,788,983 | A | 8/1998 | Chien et al. |
| 5,840,566 | A | 11/1998 | Kourides et al. |
| 6,114,144 | A | 9/2000 | Kourides et al. |
| 6,117,991 | A | 9/2000 | Wondisford et al. |
| 6,284,491 | B1 | 9/2001 | Wondisford et al. |
| 6,306,434 | B1 | 10/2001 | Hong et al. |
| 6,342,221 | B1 | 1/2002 | Thorpe et al. |
| 6,365,127 | B1 | 4/2002 | Kourides et al. |
| 6,365,146 | B1 | 4/2002 | Uhrich |
| 2001/0053538 | A1 | 12/2001 | Wondisford et al. |
| 2003/0198596 | A1 | 10/2003 | Kourides et al. |
| 2004/0132137 | A1 | 7/2004 | Wondisford et al. |
| 2006/0148005 | A1 | 7/2006 | Wondisford et al. |

FOREIGN PATENT DOCUMENTS

| | | |
|---|---|---|
| EP | 0 228 604 A2 | 7/1987 |
| EP | 0 228 604 A3 | 7/1987 |
| WO | WO 90/08528 A1 | 8/1990 |
| WO | WO 2005/047319 A1 | 5/2005 |

OTHER PUBLICATIONS

Accession P0129 in the NCBI GenBank Protein Database, created 1986, 3 pages as printed.*
Ferrer-Costa (2007. J Mol Biol. 365: 249-256).*
Wells (1990) Biochemistry 29(37): 8509-8517.*
Ngo et al (1994) "The Protein Folding Problem and Tertiary Structure Prediction, Chapter 14: Computational Complexity Protein Structure Prediction, and the Levinthal Paradox" pp. 433-440 and 492-495 only.*
Bork (2000) Genome Research 10:398.*
Skolnick et al (2000) Trends in Biotech. 18(1): 34.*
Doerks et al (1998) Trends in Genetics 14(6): 248.*
Brenner (1999) Trends in Genetics 15(4): 132.*
Bruyette, "Feline Hyperthyroidism," World Congress [online]. World Small Animal Veterinary Association World Congress, Vancouver, BC, Canada, Aug. 8-11, 2001 [retrieved on Nov. 5, 2003]. Retrieved from the Internet:<URL:www.vin.com/VINDBPub/SearchPB/Proceedings/PRO5000/PR00107.htm>; 5 pgs.
Huysmans et al., "Administration of a Single Low Dose of Recombinant Human Thyrotropin Significantly Enhances Thyroid Radioiodide Uptake in Nontoxic Nodular Goiter," *The Journal of Clinical Endocrinology & Metabolism*, Oct. 2000; 85(10):3592-3596.
Narayan et al., "Functional Expression of Yoked Human Chorionic Gonadotropin in Baculovirus-Infected Insect Cells," *Molecular Endocrinology*, Dec. 1995; 9(12):1720-1726.
National Center for Biotechnology Information, GenBank Locus AF160250, Accession No. AF160250, "Canis familiaris thyrotropin alpha subunit mRNA, complete cds." [online] Bethesda, MD [retrieved on Oct. 2, 2006]. Retrieved from Internet:<http://www.ncbi.nlm.nih.gov/entrez/viewer.fcgi?db=nucleotide
&val=5360187>; 2 pages.
National Center for Biotechnology Information, GenBank Locus AF354939, Accession No. AF354939, "Panthera tigris altaica glycoprotein hormone alpha subunit (GPH) mRNA, complete cds." [online] Bethesda, MD [retrieved on Oct. 2, 2006]. Retrieved from the Internet: <http://www.ncbi.nlm.nih.gov/entrez/viewer.fcgi?db=nucleotide&val=13561973>; 2 pages.
National Center for Biotechnology Information, GenBank Locus AF408393, Accession No. AF408393, "Panthera tigris altaica glycoprotein hormone alpha subunit precursor, mRNA, complete cds." [online] Bethesda, MD [retrieved on Oct. 3, 2006]. Retrieved from the Internet: <http://www.ncbi.nlm.nih.gov/entrez/viewer.fcgi?db=nucleotide&val=22535904>; 2 pages.

(Continued)

*Primary Examiner*—Bridget E Bunner
*Assistant Examiner*—Zachary C Howard
(74) *Attorney, Agent, or Firm*—Mueting Raasch & Gebhardt, P.A.

(57) ABSTRACT

Amino acid sequences of feline thyrotropin and polynucleotide sequences encoding feline thyrotropin are provided, as well as methods of making and using said sequences.

31 Claims, 10 Drawing Sheets

OTHER PUBLICATIONS

National Center for Biotechnology Information, GenBank Locus AY972823, Accession No. AY972823, "Felis catus thyrotropin alpha mRNA, complete cds." [online] Bethesda, MD [retrieved on Oct. 2, 2006]. Retrieved from the Internet:<http://www.ncbi.nlm.nih.gov/entrez/viewer.fcgi?db=nucleotide&val=62530408>; 2 pages.

National Center for Biotechnology Information, GenBank Locus AY972824, Accession No. AY972824, "Felis catus thyrotropin beta (TSHB) gene, complete cds." [online] Bethesda, MD [retrieved on Oct. 2, 2006]. Retrieved from the Internet: <http://www.ncbi.nlm.nih.gov/entrez/viewer.fcgi?db=nucleotide&val=62530410>; 2 pages.

National Center for Biotechnology Information, GenBank Locus P54828, Accession No. P54828, "Thyrotropin beta chain precursor (Thyroid-stimulating hormone beta subunit) (TSH-beta) (TSH-B)." [online] Bethesda, MD [retrieved on Oct. 2, 2006]. Retrieved from the Internet:<http://www.ncbi.nlm.nih.gov/entrez/viewer.fcgi?db=protein&val=1717805>; 3 pages.

National Center for Biotechnology Information, GenBank Locus Q9SXW8, Accession No. Q9SXW8, "Chlorophyll a/b-binding protein." [online] Bethesda, MD [retrieved on Oct. 2, 2006]. Retrieved from the Internet:<http://www.ncbi.nlm.nih.gov/entrez/viewer.fcgi?db=protein&val=75266683>; 2 pages.

National Center for Biotechnology Information, GenBank Locus CFU51644, Accession No. U51644, "Canis familiaris thyrotropin beta chain mRNA, complete cds." [online] Bethesda, MD [retrieved on Oct. 2, 2006]. Retrieved from the Internet:<http://www.ncbi.nlm.nih.gov/entrez/viewer.fcgi?db=nucleotide&val=1263292>; 2 pages.

Nguyen et al., "Cloning of the Cat TSH Receptor and Evidence Against an Autoimmune Etiology of Feline Hyperthyroidism," *Endocrinology*, 2002; 143(2):395-402.

Rayalam et al., "Recombinant Feline Thyrotropin (fTSH): Immunological Detection and Bioactivity," Abstract, Fifth Annual Georgia Graduate Student Interdisciplinary Conference, Feb. 11-12, 2005; University of Georgia, Athens, GA, title page, Table of Contents, partial schedule for Saturday, Feb. 12, and p. 20.

Rayalam et al., "Cloning and sequencing of feline thyrotropin (fTSH): Heterodimeric and yoked constructs," Abstract, Proceedings of the 23$^{rd}$ Veterinary Medical Forum, American College of Veterinary Internal Medicine, Baltimore, MD; Jun. 1-4, 2005.

Rayalam et al., "Expression and purification of feline thyrotropin (fTSH): Immunological detection and bioactivity of heterodimeric and yoked glycoproteins," Abstract, Proceedings of the 23$^{rd}$ Veterinary Medical Forum, American College of Veterinary Internal Medicine, Baltimore, MD; Jun. 1-4, 2005.

Rayalam et al., "Cloning and sequencing of feline thyrotropin (fTSH): Heterodimeric and yoked constructs," *Domestic Animal Endocrinology*, Mar. 2006; 30:203-217. Published on-line Aug. 9, 2005.

Rayalam et al., "Expression and purification of feline thyrotropin (fTSH): Immunological detection and bioactivity of heterodimeric and yoked glycoproteins," *Domestic Animal Endocrinology*, Mar. 2006; 30:185-202. Published on-line Aug. 10, 2005.

Barany and Merrifield (Gross and Meienhofer, Eds.) *The Peptides* vol. 2 Academic Press: City, State; 1980. Title page, publisher's page and table of contents only.

Ben-Menahem et al., "The position of the alpha and beta subunits in a single chain variant of human chorionic gonadotropin affects the heterodimeric interaction of the subunits and receptor-binding epitopes," *J. Biol. Chem.*, 2001; 276:29871-29879.

Broome et al., "Predictive value of tracer studies for 131I treatment in hyperthyroid cats," *Am. J. Vet. Res.*, 1988; 49(2):193-197.

Carter et al., "Humanization of an anti-p185HER2 antibody for human cancer therapy," *Proc. Nat'l Acad. Sci. USA*, 1992; 89:4285-4289.

Chard et al., "Fluoroimmunoassay for human choriomammotropin," *Clinical Chemistry*, 1979; 25(6):973-975.

Chin et al., "Nucleotide sequence of the mRNA encoding the pre-alpha-subunit of mouse thyrotropin," *Proc. Natl. Acad. Sci. USA*, 1981; 78:5329-5333.

Clark-Lewis et al., "Chemical synthesis, purification, and folding of C-X-C and C-C chemokines," *Meth. Enzymol.*, 1997; 287:233-250.

Coligan et al. (Eds.), "Chapter 9: Peptides" *Current Protocols in Immunology*, vol. 3. John Wiley & Sons, Inc: Somerset, NJ; 1991. Title page, publisher's page, and table of contents.

Coligan et al. (Eds.), "Chapter 2: Induction of Immune Responses (Section II 'Production of Antibodies' and Section III 'Purification and Fragmentation of Antibodies')" *Current Protocols in Immunology*, John Wiley & Sons, Inc: Somerset, NJ; 1991. Title page, publisher's page, table of contents, and sections 2.8.1-2.8.10 and 2.10.1-2.10.4.

Crichton et al., "Efficacy of porcine gonadotropins for repeated stimulation of ovarian activity for oocyte retrieval and in vitro embryo production and cryopreservation in Siberian tigers (*Panthera tigris altaica*)," *Biol. Reprod.*, 2003; 68(1):105-113.

Croyle et al., "Analysis of the organization and nucleotide sequence of the chromosomal gene for the beta-subunit of rat thyrotropin," *DNA*, 1986; 5:299-304.

Erwin et al., "Nucleotide sequence of cloned complementary deoxyribonucleic acid for the alpha subunit of bovine pituitary glycoprotein hormones," *Biochemistry*, 1983; 22:4856-2860.

Ferguson, "Early Detection of Hyperthyroidism," Meeting Abstract. Morris Animal Health Foundation: A Healthier Tomorrow for Animals 2001 Annual Meeting. Lake Tahoe, Nevada Jun. 7-9, 2001. Available online [retrieved Dec. 6, 2006]. Retrieved from the Internet: <http://web.archive.org/web/20011101225158/www.morrisanimalfoundation.org/feline_studies.html>; 6 pgs.

Fiddes et al., "Isolation, cloning and sequence analysis of the cDNA of the alpha-subunit of human chorionic gonadotropin," *Nature*, 1979; 281:351-356.

Gesundheit et al., "Mechanisms and regulation of TSH glycosilation," *Adv. Exp. Biol.*, 1986; 205:87-105.

Gharib et al., "Molecular biology of the pituitary gonadotropins," *Endocrine Reviews*, 1990; 11:177-199.

Godine et al., "α-Subunit of rat pituitary glycoprotein hormones. Primary structure of the precursor determined from the nucleotide sequence of cloned cDNAs," *J. Biol. Chem.*, 1982; 257:8368-8371.

Graham et al., "The Measurement of Feline Thyrotropin (TSH) Using a Commercial Canine Immunoradio-Metric Assay." 18$^{th}$ Annual ACVIM Forum: Abstract No. 59. Seattle, WA. May 25-28, 2000.

Gram et al., "In vitro selection and affinity maturation of antibodies from a naive combinatorial immunoglobulin library," *Proc. Natl. Acad. Sci.*, 1992; 89:3576-3580.

Green et al. (Manson ed.) "Production of Polyclonal Antisera" *Immunochemical Protocols*, Humana Press: Totowa, NJ; 1992. Title page, publisher's page, table of contents, and pp. 1-5.

Green et al., "Antigen-specific human monoclonal antibodies from mice engineered with human Ig heavy and light chain YACs," *Nature Genet.*, 1994; 7:13-21.

Harlow et al., *Antibodies: A Laboratory Manual*, Cold Spring Harbor Laboratory Press: Cold Spring Harbor, NY; 1988. Title page, publisher's page, table of contents and pp. 319, 726.

Hayashizaki et al., "Molecular cloning of the human thyrotropin-beta subunit gene," *FEBS Lett.*, 1985; 188:394-400.

Hoenig et al., "Assessment of thyroid functional reserve in the cat by the thyrotropin-stimulation test," *Amer. J. Vet. Res.*, 1983; 44:1229-1232.

Hollister et al., "Engineering lepidopteran insect cells for sialoglycoprotein production by genetic transformation with mammalian β-1,4-galactosyltransferase and α-2,6-sialyltransferase genes," *Glycobiology*, 2001; 11(1):1-9.

Hollister et al., "Evidence for a sialic acid salvaging pathway in lepidopteran insect cells," *Glycobiology*, 2003; 13(6):487-495.

Jones et al., "Replacing the complementarity-determining regions in a human antibody with those from a mouse," *Nature*, 1986; 321:522-525.

Kay et al., *Phage display of peptides and proteins: A laboratory manual*, Academic Press: San Diego, CA; 1996. Title page, publisher's page, and table of contents.

Kermani et al., "Production of ScFv antibody fragments following immunization with a phage-displayed fusion protein and analysis of reactivity to surface-exposed epitopes of the protein F of *Pseudomonas aeruginosa* by cytofluorometry," *Hybridoma*, 1995; 14:323-328.

Kohler et al., "Continuous cultures of fused cells secreting antibody of predefined specificity," *Nature*, 1975; 256:495-497.

Lapthorn et al., "Crystal structure of human chorionic gonadotropin," *Nature*, 1994; 369:455-461.

Lonberg et al., "Antigen-specific human antibodies from mice comprising four distinct gene modifications," *Nature*, 1994; 368:856-859.

Martin et al., "Evaluation of dietary and environmental risk factors for hyperthyroidism in cats," *J. Am Vet. Med. Assoc.*, 2000; 217(6):853-856.

Maurer et al., "The sequence of a cloned cDNA for the beta subunit of bovine thyrotropin predicts a protein containing both $NH_2$- and COOH-terminal extensions," *J. Biol. Chem.*, 1984; 259:5024-5027.

Mayer et al. (Eds.), *Immunochemical Methods in Cell and Molecular Biology*. Elsevier, Inc: New York, NY; 1987. Title page, publisher's page and table of contents only.

Meienhofer et al. (Li, Ed.), *Hormonal Proteins and Peptides*, Academic Press: New York NY; 1973; vol. 2. Title page, publisher's page and table of contents only.

Merrifield, "Solid Phase Peptide Synthesis. I. The Synthesis of a Tetrapeptide" 1963 *J. Am. Chem. Soc.* 85:2149.-2154.

Merrifield, "Automated Synthesis of Peptides," 1965 *Science* 150(693):178-185.

Merrifield, "Solid Phase Synthesis," 1986 *Science* 232(4787):341-347.

Morrison, "Immunology: Success in Specification." 1994 *Nature* 368:812-813.

National Center for Biotechnology Information, National Library of Medicine, National Institutes of Health, GenPept Locus P54828, Accession No. P54828, "Thyrotropin subunit beta precursor (Thyroid-stimulating hormone subunit beta) (TSH-beta) (TSH-B) (Thyrotropin beta chain)," [online]. Bethesda, MD [retrieved on Oct. 4, 2007]. Retrieved from the Internet:<http://www.ncbi.nlm.nih.gov/entrez/viewer.fcgi?db=protein&val=1717805>; 3 pgs.

O'Brien et al., "The cloning and expression of the alpha subunit of equine glycoprotein hormones," *Biochem. Soc. Trans.*, 1995; 23:347S.

Olson et al., "Production of a biologically active variant form of recombinant human secretin," *Peptides*, 1988; 9:301-307.

Orlandi et al., "Cloning immunoglobulin variable domains for expression by the polymerase chain reaction," *Proc. Nat'l. Acad. Sci. USA*, 1989; 86:3833-3837.

Patel, "Glycoprotein Hormones: A Clasped Embrace." 1994 *Nature* 369:438-439.

Porter, "The hydrolysis of rabbit γ-globulin and antibodies with crystalline papain," *Biochem. J.*, 1959; 73:119-126.

Rayalam, Srujana "Cloning, Expression, and Purificaion of Recombinant Feline Thyrotropin (fTSH): Effect of Glycosylation on Immunoreactivity." PhD Thesis: available Oct. 9, 2006.

Riechmann et al., "Reshaping human antibodies for therapy," *Nature*, 1988; 332:323-327.

Sairam et al., "A role for glycosilation of the alpha subunit in transduction of biological signal in glycoprotein hormones," *Science*, 1985; 229:65-67.

Sambrook et al., *Molecular Cloning: A Laboratory Manual*, 3$^{rd}$ ed., Cold Spring Harbor Laboratory Press: Cold Spring Harbor, NY; 2001. Title page, publisher's page, and table of contents.

Sandhu, "Protein engineering of antibodies," *Crit, Rev. Biotech.*, 1992; 12:437-462.

Sanna et al. "Directed selection of recombinant human monoclonal antibodies to herpes simplex virus glycoproteins form phage display libraries," *Proc. Natl. Acad. Sci.*, 1995; 92:6439-6443.

Schmitz et al., "Phage display: a molecular tool for the generation of antibodies—a review," *Placenta*, 21 Suppl., 2000; S106-12.

Seelan et al., "Structural organization and promoter analysis of the bovine cytochrome c oxidase subunit VIIc gene. A functional role for YY1," *J. Biol. Chem.*, 1997; 272:10175-10181.

Singer et al., "Optimal humanization of 1B4, an anti-CD 18 murine monoclonal antibody, is achieved by correct choice of human V-region framework sequences," *J. Immunol.*, 1993; 150:2844-2857.

Stewart et al., *Solid Phase Peptide Synthesis*, W.H.Freeman Co., San Francisco, 1969. Title page, publisher's page and table of contents only.

Studer et al., "Natural heterogeneity of thyroid cells: the basis for understanding thyroid function and nodular goiter growth,"1989 *Endocrine Rev*, 10(2):125-135.

Tatusova et al., "BLAST 2 Sequences, a new tool for comparing protein and nucleotide sequences," *FEMS Microbiol. Lett.*, 1999; 174:247-250.

Taylor et al., "Human immunoglobulin transgenes undergo rearrangement, somatic mutation and class switching in mice that lack endogenous IgM," *Int. Immunol.*, 1994; 6:579-591.

Tessier et al., "Enhanced secretion from insect cells of a foreign protein fused to the honeybee melittin signal peptide," *Gene*, 1991; 98(2):177-183.

Thompson et al., "CLUSTAL W: Improving the sensitivity of progressive multiple sequence alignment through sequence weighting, position-specific gap penalties and weight matrix choice," *Nucl. Acids Res.*, 1994; 22:4673-4680.

Thotakura et al., "Structure-function studies of oligosaccharides of recombinant human thyrotropin by sequential deglycosylation and resialyation," *Glycobiology*, 1994; 4:525-533.

Thotakura et al., "Glycoprotein hormones: glycobiology of gonadotropins, thyrotropin and free alpha subunit," *Glycobiology*, 1995; 5:3-10.

Verhoeyen et al., "Reshaping human antibodies: grafting an antilysozyme activity," *Science*, 1988; 239:1534-1536.

Ward et al. (Committee on Methods of Producing Monoclonal Antibodies) *Monoclonal Antibody Production*, Institute for Laboratory Animal Research, National Research Council, The National Academy Press: Washington, D.C.; 1999. Title page, publisher's pgs., preface, and table of contents.

Williams et al., "Validation of an immunoassay for canine thyroid-stimulating hormone and changes in serum concentration following induction of hypothyroidism in dogs," *J. Am. Vet. Med. Assoc.*, 1996; 209:1730-1732.

Wolf et al., Expression of the gene for the beta subunit of mouse thyrotropin results in multiple mRNAs differing in their 5'-untranslated regions, *J. Biol. Chem.*, 1987; 262:16596-16603.

Wondisford et al., "Isolation and characterization of the human thyrotropin beta-subunit gene. Differences in gene structure and promoter function from murine species," *J. Biol. Chem.*, 1988; 263:12538-12542.

Yang, "Cloning of canine, equine and ovine thyrotropin genes and production of recombinant canine thryrotropin," University of Georgia, PhD Thesis: available Jul. 29, 1997.

Yang et al., "Canine thyrotropin beta-subunit gene: cloning and expression in *Escherichia coli*, generation of monoclonal antibodies, and transient expression in the Chinese hamster ovary cells," *Domestic Animal Endocrinology*, 2000; 18(4):363-78.

Yang et al., "cDNA cloning of canine common alpha gene and its co-expression with canine thyrotropin beta gene in baculovirus expression system," *Domestic Animal Endocrinology*, 2000; 18(4):379-93.

Zerfaoui et al., "Glycosylation is the structural basis for changes in polymorphism and immunoreactivity of pituitary glycoprotein hormones," *Eur. J. Clin. Chem and Clin. Biochem.*, 1996; 34:749-753.

\* cited by examiner

Construct of Feline Thyrotropin-beta Subunit with First Intron

```
1                                                              30
5'(GAA TTC)ATG ACT GCT ATC TAC CTG ATG TCC GTG CTT
         met thr ala ile tyr leu met ser val leu
31                                                             75
TTT GGC CTG GCA TGT GGA CAA GCG ATG TCT TTT TGT TTT CCA ACT
phe gly leu ala cys gly gln ala met ser phe cys phe pro thr
76                                                            120
GAG TAT ATG ATG CAT GTC GAA AGG AAA GAG TGT GCT TAT TGC CTA
glu cys met met his val glu arg lys glu cys ala tyr cys leu
121                                                           162
ACC ATC AAC ACC ACC ATC TGT GCT GGA TAT TGT ATG ACA CGG
thr ile asn thr thr ile cys ala gly tyr cys met thr arg
```

*Intron 1*

*163 GTATGTAGTTCATCTCACTTCTTTTAGCTGAAAATTAGATAAACCTAGACT*
*CAGTCCATTTCTATCCAGAAAGGAAATGAGATAAATCACAACCTCATTTCACAGACCTAAC*
*GGTCATTGGCTCCTTAGAGGTAGAGTCCCTAGGTTATAATATACGGACCTACTCCATACAG*
*TTGGTACAGATAATTTTTACAATAGTTTTACTCCCAAAGTTTATTTAAACCTTATCTTGTTCC*
*CACGATCAAGGATAAAAGAGAGGTGTGTGTGTATGTCATTTTTTTTGTCTCTATAGGATT*
*CAGTGTGGATATGCTGAATTGGTATTGGGGAATGGGACTAAGGAATCCTCCCCCAGTCCTA*
*TTTGTATCTATGGGATGTAAGCGAATTAACATTTTGCTTCCTCTTCTGTGCTTCCCTCAG*
*580*

```
581                                                           625
GAT ATC AAT GGC AAA CTG TTT CTT CCC AAA TAT GCT CTG TCC CAA
asp ile asn gly lys leu phe leu pro lys tyr ala leu ser gln
626                                                           670
GAT GTT TGC ACC TAC AGA GAC TTC CTG TAC AAG ACT GTA GAA ATA
asp val cys thr tyr arg asp phe leu tyr lys thr val glu ile
671                                                           715
CCA GGA TGC CCA CAC CAT GTT ACT CCC TAT TTC TCC TAC CCG GTA
pro gly cys pro his his val thr pro tyr phe ser tyr pro val
716                                                           760
GCT GTA AGC TGT AAA TGT GGC AAG TGT AAT ACT GAC TAT AGC GAC
ala val ser cys lys cys gly lys cys asn thr asp tyr ser asp
761                                                           805
TGC ATA CAT GAG GCC ATC AAG ACA AAT GAT TGT ACC AAA CCC CAG
cys ile his glu ala ile lys thr asn asp cys thr lys pro gln
806                                  835
AAG TCC GAT GTG GTA GGA GTT TCT ATC TAA (GCGGCCGC(4))(AT)5-3'
lys ser asp val val gly val ser ile stop
```

( ) denotes the Eco RI restriction sites
Bold denotes signal sequence
*Bold/italic* denotes the intron 1 sequence

*Fig. 1*

Feline Thyrotropin Alpha Subunit Construct

Bold denotes 24 amino acid unexpressed signal sequence as per structure in other species
*Bold italics* denotes sequence upstream from expressed but not secreted signal sequence; only reported in equine; whether it is expressed is not clear.
( ) denotes Eco R1 restriction site from TOPO Blunt vector
Underlined denotes additional sequence from TOPO Blunt vector
( ($_1$)) denotes Factor XA site
( ($_2$)) denotes Flag tag
( ($_3$)) denotes stop codon
( ($_4$)) denotes Not1 restriction enzyme site
( )$_5$ denotes extra bases needed for restriction enzyme to work

*Fig. 2*

(GAATTC) GCCCTT

| 1 | | | | | | | | | | | | | | | 45 |
|---|---|---|---|---|---|---|---|---|---|---|---|---|---|---|---|

*AGT TAC TGA GAA ATC ACA AGA CGA AGC CAA AAT CCC TCT TCA GAT*
ser tyr OPA glu ile thr arg arg ser gln asn pro ser ser asp 46                                                                                      90
*CCA CGG TCA ACT GCC CTG ATC ACA TCC TGC AAA AAG TCC GGA GGA*
pro arg ser thr ala leu ile thr ser cys lys lys ser gly gly 91                                                                                      135
*AGG AGA GCC ATG GAT TAC TAC AGA AAA TAT GCA GCT GTC ATT CTG*
arg arg ala met asp tyr tyr arg lys tyr ala ala val ile leu 136                                                                                     180
GCC ATA CTC TCT GTG TTT CTG CAT ATT CTC CAT TCT TTT CCT GAT
ala ile leu ser val phe leu his ile leu his ser phe pro asp 181                                                                                     225
GGA GAG TTT ACA ATG CAG GGG TGC CCA GAA TGC AAG CTA AAG GAA
gly glu phe thr met gln gly cys pro glu cys lys leu lys glu 226                                                                                     270
AAC AAA TAC TTC TCC AAG TTG GGT GCC CCA ATT TAT CAA TGC ATG
Asn lys tyr phe ser lys leu gly ala pro ile tyr gln cys met 271                                                                                     315
GGC TGC TGC TTC TCC AGA GCA TAC CCC ACT CCA GCA AGG TCC AAG
gly cys cys phe ser arg ala tyr pro thr pro ala arg ser lys 316                                                                                     360
AAG ACA ATG TTG GTC CCA AAG AAC ATC ACC TCA GAA GCC ACA TGC
lys thr met leu val pro lys asn ile thr ser glu ala thr cys 361                                                                                     405
TGT GTG GCC AAA GCC TTT ACC AAG GCC ACG GTA ATG GGA AAT GCC
cys val ala lys ala phe thr lys ala thr val met gly asn ala

Fig. 2a 406                                                                                              450
AAA GTG GAG AAT CAC ACA GAG TGC CAC TGC AGC ACT TGC TAT CAC lys   val   glu   asn   his   thr   glu   cys   his   cys   ser   thr   cys   tyr   his 451           459                                                                    492
CAC AAG ATT (ATC GAA GGT CGT$_{(1)}$)(GAC TAC AAG GAC GAT GAC GAT his   lys   ile   ile   glu   gly   arg   asp   tyr   lys   asp   asp   asp   asp 493 495                              510
AAG$_{(2)}$) (TAA$_{(3)}$) (GCGGCCGC$_{(4)}$)(TATG)$_5$ 3' lys

Fig. 2b

Yoked Feline Thyrotropin

| Fig. 3a |
| --- |
| Fig 3b |

( ) denotes the Eco RI restriction sites
Bold denotes signal sequence
*Bold italics* denotes intron 1 sequence  1=Factor XA site
( ($_1$)) denotes Factor XA site
( ($_2$)) denotes Flag tag
( ($_3$)) denotes stop codon
( ($_4$)) denotes Not1 restriction enzyme site
( )$_5$ denotes extra bases needed for restriction enzyme to work

*Fig. 3*

```
1                                                      30
5'(GAA TTC)ATG ACT GCT ATC TAC CTG ATG TCC GTG CTT
         met thr ala ile tyr leu met ser val leu
31                                                     75
TTT GGC CTG GCA TGT GGA CAA GCG ATG TCT TTT TGT TTT CCA ACT
phe gly leu ala cys gly gln ala met ser phe cys phe pro thr
76                                                     120
GAG TAT ATG ATG CAT GTC GAA AGG AAA GAG TGT GCT TAT TGC CTA
 glu cys met met his val glu arg lys glu cys ala tyr cys leu
121                                           162
ACC ATC AAC ACC ACC ATC TGT GCT GGA TAT TGT ATG ACA CGG
 thr ile asn thr thr ile cys ala gly tyr cys met thr arg
```

*Intron 1*

*163 GTATGTAGTTCATCTCACTTCTTTTAGCTGAAAATTAGATAAACCTAGACT*
*CAGTCCATTTCTATCCAGAAAGGAAATGAGATAAATCACAACCTCATTTCACAG*
*ACCTAACGGTCATTGGCTCCTTAGAGGTAGAGTCCCTAGGTTATAATATACGGA*
*CCTACTCCATACAGTTGGTACAGATAATTTTTACAATAGTTTTACTCCCAAAGTT*
*TATTTAAACCTTATCTTGTTCCCACGATCAAGGATAAAAGAGAGGTGTGTGTGT*
*ATGTCATTTTTTTTTGTCTCTATAGGATTCAGTGTGGATATGCTGAATTGGTATT*
*GGGGAATGGGACTAAGGAATCCTCCCCCAGTCCTATTTGTATCTATGGGATGT*
*AAGCGAATTAACATTTTGCTTCCTCTTCTGTGCTTCCCTCAG     580*

```
581                                                    625
GAT ATC AAT GGC AAA CTG TTT CTT CCC AAA TAT GCT CTG TCC CAA
 asp ile asn gly lys leu phe leu pro lys tyr ala leu ser gln
626                                                    670
GAT GTT TGC ACC TAC AGA GAC TTC CTG TAC AAG ACT GTA GAA ATA
 asp val cys thr tyr arg asp phe leu tyr lys thr val glu ile
671                                                    715
CCA GGA TGC CCA CAC CAT GTT ACT CCC TAT TTC TCC TAC CCG GTA
 pro gly cys pro his his val thr pro tyr phe ser tyr pro val
716                                                    760
GCT GTA AGC TGT AAA TGT GGC AAG TGT AAT ACT GAC TAT AGC GAC
 ala val ser cys lys cys gly lys cys asn thr asp tyr ser asp
761                                                    805
TGC ATA CAT GAG GCC ATC AAG ACA AAT GAT TGT ACC AAA CCC CAG
 cys ile his glu ala ile lys thr asn asp cys thr lys pro gln
806      beta-specific primer sequence *         CTP linker    850
AA|G TCC GAT GTG GTA GGA GTT TCT ATC|CAG GAC TCC TCT TCC TCA
 lys ser asp val val gly val ser ile gln asp ser ser ser ser
851                    CTP linker                      892
AAG GCC CCT TCC GCC AGC CTT CCA AGC CCA|ACG CGT|CTC CCG
 lys ala pro ser ala ser leu pro ser pro thr  arg leu pro
```

\* reverse complement in construct                    Afl III ligation site

Fig. 3ₐ

```
              893          CTP linker            alpha-specific
                                                 primer sequence   937  *
              GGG CCC TCG GAC ACC CCG ATC CTC CCA CAA TTT CCT GAT GGA GAG
              gly pro ser asp thr pro ile ile pro gln phe pro asp gly glu
              938                                                     977
              TTT ACA ATG CAG GGG TGC CCA GAA TGC AAG CTA AAG GAA
              phe thr met gln gly cys pro glu cys lys leu lys glu
              978                                                    1022
              AAC AAA TAC TTC TCC AAG TTG GGT GCC CCA ATT TAT CAA TGC ATG
              Asn lys tyr phe ser lys leu gly ala pro ile tyr gln cys met
              1023                                                   1067
              GGC TGC TGC TTC TCC AGA GCA TAC CCC ACT CCA GCA AGG TCC AAG
              gly cys cys phe ser arg ala tyr pro thr pro ala arg ser lys
              1068                                                   1112
              AAG ACA ATG TTG GTC CCA AAG AAC ATC ACC TCA GAA GCC ACA TGC
               lys thr met leu val pro lys asn ile thr ser glu ala thr cys
              1113                                                   1157
              TGT GTG GCC AAA GCC TTT ACC AAG GCC ACG GTA ATG GGA AAT GCC
              cys val ala lys ala phe thr lys ala thr val met gly asn ala
              1158                                                   1202
              AAA GTG GAG AAT CAC ACA GAG TGC CAC TGC AGC ACT TGC TAT CAC
              lys val glu asn his thr glu cys his cys ser thr cys tyr his
              1203      1211
              CAC AAG ATT (ATC GAA GGT CGT₍₁₎)(GAC TAC AAG GAC GAT GAC GAT
              his lys ile  ile glu gly arg   asp tyr lys asp asp asp asp
              1245 1247                 1262
              AAG₍₂₎) (TAA₍₃₎) (GCGGCCGC₍₄₎)(TATG)₅ 3'
              lys
                         *as written
```

Fig. 3b

RECOMBINANT GLYCOPROTEINS RELATED TO FELINE THYROTROPIN

CROSS-REFERENCE TO RELATED APPLICATIONS

This application is a U.S. National Stage of International Application No. PCT/US2004/037793, filed Nov. 12, 2004, which claims the benefit of U.S. Provisional Application Ser. No. 60/519,302, filed Nov. 12, 2003, and U.S. Provisional Application Ser. No. 60/534,205, filed Jan. 5, 2004, all of which are incorporated herein by reference in their entirety.

BACKGROUND OF THE INVENTION

Thyrotropin (thyroid stimulating hormone, TSH), chorionic gonadotropin (CG), lutropin (luteinizing hormone, LH) and follitropin (follicle stimulating hormone, FSH) are members of a glycoprotein hormone family. These hormones are structurally related heterodimers with a common alpha subunit noncovalently linked to a distinct β-subunit that confers the immunological and biological specificity of each hormone. The functional activity of TSH depends on the correct assembly of the subunits into heterodimers. It is believed that the rate-limiting step in the formation of active TSH is the rate of synthesis of the β-subunit by the pituitary thyrotrope cell.

The molecular weight of mammalian TSH can range from 28 to 30 kilodaltons, with variation being associated with heterogeneity of the oligosaccharide chains. The α-subunit has a molecular weight of approximately 14 kilodaltons and has two oligosaccharide units linked to asparagine residues. Like other glycoprotein hormones, TSH is highly glycosylated with N-linked complex carbohydrates, which account for approximately 21% and 12% of the total weight in its α and β chains respectively (Gesundheit, N., Weintraub, B D, Adv. Exp. Biol., 205, 87 (1986)). Assembly of the α- and β-subunits is necessary for the biological activity of the hormone. The β-subunit has a molecular weight of 15 kilodaltons and has one asparagine linked oligosaccharide unit. There are five disulphide bonds in the α subunit and six in the β subunit. The crystal structure of TSH has not been established yet, but the crystal structure of human CG, which is structurally related, reveals that each subunit contains a central cysteine knot and three loops, two β-hairpin loops on one side of cysteine knot and a long loop in the α subunit which contains a two turn α helix on the other side. TSH has thus been classified as a part of CKGF (Cysteine Knot like Growth Factors) superfamily (Lapthorn, et al., Nature, 369, 455 (1994)).

The carbohydrate structure of glycoproteins plays an important role in hormone assembly, secretion and action. High mannose precursor carbohydrate plays an important role in the α/β-subunit heterodimer by minimizing subunit aggregation and intracellular proteolysis. The complex final carbohydrate appears to be important in determining intrinsic biologic activity as well as the metabolic clearance rate of secreted hormone from the circulation. The carbohydrates of the common α-subunit are most important for biological activity (Sairam, M., Bhargavi, G., Science, 229, 65 (1985)). Interestingly, removal of terminal sialic acid residues of recombinant human TSH increased in vitro bioactivy of hormone (Thotakura, et al., Glycobiology, 4, 525 (1995)). The biological activity of resulting peptide showed a reduced ability to stimulate adenylate cyclase, despite still binding to its receptor with high affinity (Thotakura N, Blithe, D., Glycobiology, 5, 3 (1995)).

Thyrotropin (TSH) is produced and released by anterior pituitary gland and, through its action on the thyroid gland, plays a major role in maintaining circulating levels of thyroid hormones. Released TSH binds with membrane bound TSH receptors (TSH-R) on the cells of the thyroid gland. TSH-R is a seven-transmembrane-spanning protein that uses G-protein coupled signal transduction pathways. TSH binding to TSH-R activates the adenylyl cyclase and phosphotidylinositol systems in cells, leading to increased iodination of thyroglobulin by the thyroid. TSH also promotes thyroid cell growth, leading to the formation of a goiter if the thyroid gland is overstimulated by TSH. The thyroid makes two hormones; triiodothyronine ($T_3$) which contains three iodine atoms, and thyroxine ($T_4$) which contains four, which are influenced by TSH levels. TSH synthesis and release is primarily controlled by the concentrations of thyroid hormones (especially $T_3$) and the amount of thyroid releasing hormone (TRH) released by the hypothalamus. Thyroid hormones control, through negative feedback, the mRNA transcription of TSH, while TRH controls the glycosylation, activation, and release of TSH.

Extensive work has been done characterizing the genes and expressed proteins for the alpha and beta subunits of TSH for various species. The alpha and beta subunits are synthesized from separate mRNAs coded by DNA from genes on separate chromosomes. For example, a single gene coding for the alpha subunit of TSH has been isolated and cloned from numerous species including humans (Fiddes, J, Goodman, H. M., Nature, 281, 351 (1979)), cattle (Erwin et al., Biochemistry, 22, 4856 (1983)), rat (Godine et al., J. Biol. Chem., 257, 8368 (1982)), mouse (Chin et al., Proc. Natl. Acad. Sci. USA, 78, 5329 (1981)), horse (M, O., Headon, D., Biochem. Soc. Trans., 3, 347S (1995)), and dog (Yang et al., Domestic Animal Endocrinology, 18, 379 (2000)). This work has shown that there are two N-linked oligosaccharide chains attached to Asn56 and Asn82 and five intramolecular disulphide bonds in the α-subunit. A 24 amino acid leader sequence, which is cleared prior to secretion, is followed by a 96 amino acid mature protein in all species except the man, where the TSH α-subunit is a 92 amino acid mature protein (Gharib et al., Endocrine Reviews, 11, 177 (1990)).

The gene encoding the beta subunit of TSH has also been characterized. The gene encoding TSH β-subunit has been cloned and sequenced in humans (Hayashizaki et al., FEBS Lett., 188, 363 (1985)), cattle (Maurer et al., J. Biol. Chem., 259, 5024 (1984)), mouse (Wolf et al., J. Biol. Chem., 262, 16596, (1987)), rat (Croyle et al., DNA, 5, 299 (1986)), and dog (Yang et al., Domestic Animal Endocrinology, 18, 363 (2000)). There are three exons and two introns in the β-subunit gene. The first is only 37 base pair (bp) and untranslated followed by a 3.9 kilo base intron. The function of the first exon is unclear; however it has been speculated that exon I may interact directly with thyroid hormone and its receptor and down regulate the TSHβ gene (Wondisford et al., J. Biol. Chem. 263, 12538 (1988)). However, while there has been extensive work on both thyrotropin subunits in a variety of different species, the DNA sequences and expressed glycoproteins for feline TSH have not yet been reported.

Feline TSH has been speculated to play an important part in the pathogenesis and diagnostic tests for feline hyperthyroidism, which has been recognized as the most common endocrine disorder in cats. One out of every three hundred cats is now diagnosed for hyperthyroidism. Canned cat food, cat litter, and pesticides have been identified as possible risk factors for the disease (Martin et al., J. Am. Vet. Med. Assoc., 217(6), 853 (2000)). The most common cause of hyperthyroidism is a thyroid adenoma that produces excessive circulating concentrations of triiodothyronine ($T_3$) and thyroxine ($T_4$). Feline hypertheyroidism occurs primarily in middle-aged to older cats, and can vary from mild to severe in effect. The most common symptoms associated with feline hyperthyroidism are weight loss, hyperactivity, increased appetite, and excessive drinking and urination. Intermittent vomiting and diarrhea may also occur, as well as increased heart rate and arrhythmias. Early diagnosis of feline hyperthyroidism is preferred, as untreated hyperthyroidism can lead to kidney disease, hypertension, and diabetes, and may eventually lead to congestive heart failure. Current diagnosis of feline hyperthyroidism is based on measurement of levels of $T_3$ and $T_4$, while current therapy utilizes antithyroid drug administration, surgery, and/or the use of radioactive iodine.

A commercially available canine TSH immunoassay (Williams et al., J. Am. Vet. Med. Assoc., 209, 1730 (1996)) has been evaluated for detection of feline TSH (fTSH). Although 68% of hyperthyroid cats had TSH concentrations below the detection limit, the assay was not sensitive enough to distinguish normal from low values (Graham et al., Proceedings, 18th ACVIM Forum, Seattle, Wash., Abstract p. 719 (2000)). Therefore, peptide reagents and antibodies that are more specific for feline thyrotropin are necessary for a clinically useful immunoassay. Measurement of endogenous fTSH would allow diagnosis of early hyperthyroidism where TSH levels are suppressed by a hyperfunctioning thyroid gland. Also, a valid feline TSH assay would help characterize chemicals that might directly or indirectly influence feline thyroid physiology, potentially leading to hyperthyroidism. The problem of obtaining sufficient thyrotropin for the development of such tests is complicated by the fact that a commercially available pituitary source of fTSH does not exist.

SUMMARY OF THE INVENTION

The invention provides isolated feline thyrotropin β-subunit polypeptide, feline thyrotropin α-subunit polypeptide, feline thyrotropin yoked polypeptide, and heterodimeric feline thyrotropin. The feline thyrotropin β-subunit polypeptide can have an amino acid sequence with at least 80% identity to SEQ ID NO: 1, or optionally an amino acid sequence that consists essentially of SEQ ID NO: 1. The feline thyrotropin β-subunit polypeptide may also include a signal sequence. If it includes a signal sequence, the polypeptide may include an amino acid sequence with at least 80% identity to SEQ ID NO: 2.

The invention also provides an isolated feline thyrotropin α-subunit polypeptide including an amino acid sequence with at least 80% identity to SEQ ID NO: 3, or optionally an amino acid sequence that consists essentially of SEQ ID NO: 3. The feline thyrotropin α-subunit polypeptide may further include a signal sequence. If it has a signal sequence, the polypeptide may include an amino acid sequence with at least 80% identity to SEQ ID NO: 4.

The invention also provides an isolated feline thyrotropin yoked polypeptide including an amino acid sequence with at least 80% identity to SEQ ID NO: 5, or optionally an amino acid sequence consisting essentially of SEQ ID NO: 5. The feline thyrotropin yoked polypeptide may also include a signal sequence. If it has a signal sequence, the polypeptide may include an amino acid sequence with at least 80% identity to SEQ ID NO: 6. The invention also provides an isolated feline thyrotropin yoked polypeptide consisting essentially of SEQ ID NO: 1 and SEQ ID NO: 3 in which the polypeptide sequences are connected by a spacer peptide.

The invention also provides nucleic acid sequences encoding the various polypeptides of the invention. For instance, the invention provides an isolated polynucleotide including a nucleic acid sequence encoding the feline thyrotropin β-subunit polypeptide, or optionally a polynucleotide consisting essentially of SEQ ID NO: 7. The isolated polynucleotide encoding feline thyrotropin β-subunit polypeptide optionally includes an intron sequence and may consist essentially of SEQ ID NO: 8. The invention also provides an isolated polynucleotide comprising a nucleic acid sequence encoding feline thyrotropin α-subunit polypeptide, which optionally may be a polynucleotide consisting essentially of SEQ ID NO: 9 or SEQ ID NO: 10, in which SEQ ID NO: 10 further optionally includes a leader sequence. The invention also provides an isolated polynucleotide including a nucleic acid sequence encoding the feline thyrotropin yoked polypeptide, or optionally a polynucleotide consisting essentially of SEQ ID NO: 11. The isolated polynucleotide encoding feline thyrotropin yoked polypeptide may also include an intron sequence and optionally consists essentially of SEQ ID NO: 12.

The invention also provides a vector including one or more of a polynucleotide encoding a feline thyrotropin β-subunit polypeptide, a feline thyrotropin α-subunit polypeptide, or a feline thyrotropin yoked polypeptide according to the invention. The vector can be a cloning vector or an expression vector. If it is an expression vector, the vector preferably further includes a regulatory sequence operably linked to the polynucleotide. The vector may be viral or non-viral, and the vector may be integrating or non-integrating.

The invention also provides an isolated antibody that specifically binds to a feline thyrotropin polypeptide. The feline thyrotropin polypeptide may be the feline thyrotropin β-subunit polypeptide, the feline thyrotropin α-subunit polypeptide, or the feline thyrotropin yoked polypeptide, in which the yoked polypeptide may or may not include the CTP spacer peptide. The antibody may be a monoclonal antibody, and further may be a humanized monoclonal antibody. Alternately, the antibody may be a polyclonal antibody.

The invention further provides a method of detecting physiological levels of feline thyrotropin in a sample. This method includes obtaining a sample from a cat to be tested, contacting the sample with an antibody of the invention, and assessing complex formation between the antibody and feline thyrotropin. The feline sample used in the method may be a bodily fluid. In one aspect, the method may use a sandwich-type immunoassay. In a further aspect, the method may be used to diagnose a feline thyroid disorder. The feline thyroid disorder being diagnosed may be feline hyperthyroidism.

The invention also provides a method of treating a mammal suspected of having hyperthyroidism. This method involves administering to the mammal a feline thyrotropin heterodimer including the feline thyrotropin α-subunit and β-subunit polypeptide, or a feline thyrotropin yoked polypeptide. The mammal treated by this method may be a cat. The method may further include the aspect of sensitizing the thyroid to increase the response of the thyroid to ablative treatment with radioiodide.

The invention also provides a pharmaceutical composition that includes a pharmaceutically acceptable carrier and a feline thyrotropin heterodimer including feline thyrotropin α-subunit and β-subunit polypeptide, or a feline thyrotropin yoked polypeptide. The pharmaceutical composition may be formulated as a single unit dosage.

The invention also provides a transgenic eukaryotic cell that includes one or more of a polynucleotide that encodes a feline thyrotropin β-subunit polypeptide, a feline thyrotropin α-subunit polypeptide, or a feline thyrotropin yoked polypeptide, which may include a CTP spacer peptide or another suitable spacer peptide. The transgene nucleotide sequences can be genomically integrated or they can be extrachromosomal. The eukaryotic cell may be, for example, an insect cell derived from *Spodoptera frugiperda*, a Chinese Hamster Ovary cell, or a human embryonic kidney cell. In one aspect, the transgenic eukaryotic cell may stably expresses the feline thyrotropin α-subunit polypeptide. If the transgenic eukaryotic cell expresses the feline thyrotropin α-subunit polypeptide, it may further include a polynucleotide comprising a nucleic acid sequence encoding a β-subunit polypeptide from follicle stimulating hormone or luteinizing hormone.

The invention also includes a method for making a feline thyrotropin polypeptide that includes transfecting a eukaryotic cell with a polynucleotide encoding a feline thyrotropin polypeptide of the invention and expressing the polynucleotide encoding a feline thyrotropin polypeptide in the eukaryotic cell. This method may further include purifying the expressed feline thyrotropin polypeptide. The cell used in this method may be, for example, an insect cell derived from *Spodoptera frugiperda*, a Chinese hamster ovary cell, or a human embryonic kidney cell. One aspect of this method includes making a feline thyrotropin heterodimer which further includes the step of transfecting the cell with vectors carrying polynucleotides that prompt the expression of feline thyrotropin β-subunit polypeptide and feline thyrotropin α-subunit polypeptide. Preferably, co-transfection is accomplished contemporaneously. In another aspect of the method, the cell stably expresses feline thyrotropin α-subunit polypeptide.

The invention also includes a method preparing pituitary glycoproteins that includes transfecting a eukaryotic cell with a polynucleotide encoding a feline thryotropin α-subunit polypeptide; transfecting the eukaryotic cell with a polynucleotide encoding a β-subunit polypeptide from follicle stimulating hormone or luteinizing hormone; and expressing the polynucleotides to yield a pituitary glycoprotein.

The invention also provides a method of using a feline thyrotropin polypeptide as an immunoassay standard. The feline thyrotropin polypeptide used as an immunoassay standard may be a thyrotropin β-subunit polypeptide, a thyrotropin α-subunit polypeptide, a thyrotropin yoked polypeptide, or a feline thyrotropin heterodimer including a thyrotropin β-subunit polypeptide and a thyrotropin α-subunit polypeptide.

BRIEF DESCRIPTION OF THE DRAWINGS

FIG. 1 diagrams the sequence information of the feline thyrotropin β-subunit, with an optional intron section. Both the nucleotide sequence and the expressed amino acid sequence are shown. Starting from the 5' end of the sequence, the first 6 nucleotide bases (not numbered) represent the Eco RI restriction site. Near the middle of the nucleotide sequence is a set of nucleotides (nucleotides 163 to 580) that represent Intron 1. SEQ ID NO: 14 encompasses the entire nucleotide sequence in FIG. 1. SEQ ID NO: 7 is the nucleotide sequence running from nucleotide 1 to nucleotide 835, but lacking the nucleotides of Intron 1. SEQ ID NO: 8 is the nucleotide sequence running from nucleotide 1 to nucleotide 835 and including the Intron 1 nucleotides. SEQ ID NO: 1 is the amino acid sequence for the thyrotropin β-subunit without the signal sequence. It begins with a phenylalanine (phe) encoded by nucleotides 61 to 63, and ends with isoleucine (ile) encoded by nucleotides 830 to 832. SEQ ID NO: 2 is the amino acid sequence for the thyrotropin β-subunit prepeptide that includes the signal sequence. It begins with a methionine (met) encoded by nucleotides 1 to 3, and ends with isoleucine (ile) encoded by nucleotides 830 to 832.

FIG. 2 diagrams the sequence information of the feline thyrotropin α-subunit. Both the nucleotide sequence and the expressed amino acid sequence are shown. Starting from the 5' end of the sequence, the first 6 nucleotide bases (not numbered) represent the Eco RI restriction site, while the next 6 nucleotide bases (also not numbered) represent a TOPO Blunt vector. SEQ ID NO: 15 encompasses the entire nucleotide sequence in FIG. 2. ID NO: 9 is the nucleotide sequence running from nucleotide 100 to 459, encoding the feline thyrotropin α-subunit prepeptide, and ending immediately before the FLAG tag site and Factor Xa cleavage site. SEQ ID NO: 10 is the nucleotide sequence running from nucleotide 1 to 459, encoding the prepeptide described above as well as including a leader sequence that provides enhanced levels of construct expression. SEQ ID NO: 3 is the amino acid sequence for the thyrotropin β-subunit without the signal sequence. It begins with a phenylalanine (phe) encoded by nucleotides 172 to 174, and ends with isoleucine (ile) encoded by nucleotides 457 to 459. SEQ ID NO: 4 is the amino acid sequence for the thyrotropin β-subunit prepeptide with the signal sequence. It begins with a methionine (met) encoded by nucleotides 100 to 102, and ends with isoleucine (ile) encoded by nucleotides 457 to 459. SEQ ID NO: 16 encompasses the entire encoded peptide sequence as shown in FIG. 2.

FIG. 3 diagrams the sequence information of the yoked feline thyrotropin construct using a CTP linker consisting of the C-terminal peptide (CTP) of human chorionic gonadotropin to connect feline thyrotropin β-subunit with a feline thyrotropin α-subunit into a single chain (also known as yoked or tethered polypeptide in the literature). Both the nucleotide sequence and the expressed amino acid sequence are shown. Starting from the 5' end of the sequence, the first 6 nucleotide bases (not numbered) represent the Eco RI restriction site. Near the middle of the nucleotide sequence encoding the β-subunit is a set of nucleotides (nucleotides 163 to 580) that represent Intron 1. SEQ ID NO:17 encompasses the entire nucleotide sequence in FIG. 3. SEQ ID NO:11 is the nucleotide sequence running from nucleotide 1 to nucleotide 1211, but lacking the nucleotides of Intron 1. SEQ ID NO: 12 is the nucleotide sequence running from nucleotide 1 to nucleotide 1211 and including the Intron 1 nucleotides. SEQ ID NO: 13 is the nucleotide sequence running from nucleotide 808 to nucleotide 937, encoding the CTP spacer peptide and its two adjacent primer sequences. SEQ ID NO: 5 is the amino acid sequence for the thyrotropin yoked polypeptide without the signal sequence. It begins with a phenylalanine (phe) encoded by nucleotides 61 to 63, and ends with isoleucine (ile) encoded by nucleotides 1209 to 1211. SEQ ID NO: 6 is the amino acid sequence for the thyrotropin yoked prepeptide with the signal sequence. It begins with a methionine (met) encoded by nucleotides 1 to 3, and ends with isoleucine (ile) encoded by nucleotides 1209 to 1211. SEQ ID NO: 18 encompasses the entire encoded peptide as shown in FIG. 3.

DETAILED DESCRIPTION OF ILLUSTRATIVE EMBODIMENTS

Figure 4:
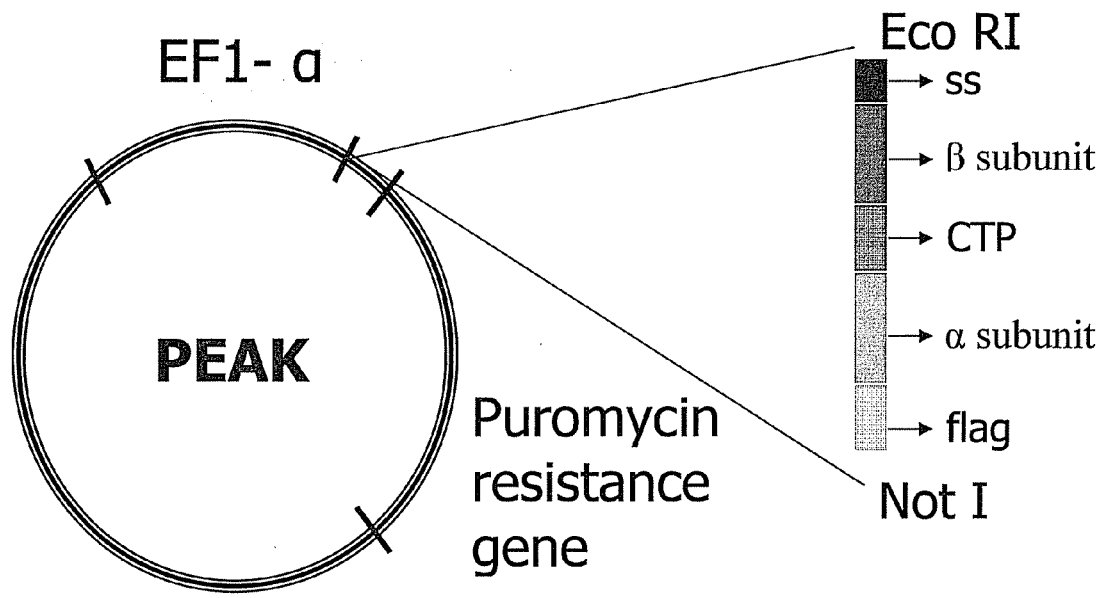
FIG. 4 shows a PEAK™ expression vector used for transforming mammalian cells to prepare yoked feline thyrotropin.

Feline thyrotropin, in vivo, is a glycoprotein heterodimer composed of alpha (α) and beta (β) subunits that are non-covalently linked. The α-subunit of feline thyrotropin is common to a variety of pituitary glycoproteins, while the β-subunit is distinct and confers the immunological and biological specificity of feline thyrotropin. The invention provides polynucleotides containing nucleic acid sequences that can be used to express feline thyrotropin, as well as the amino acid sequences of expressed feline thyrotropin polypeptides. In addition to the heterodimer form of feline thyrotropin, the invention includes the α-subunit, the β-subunit, and a yoked complex that uses a linker or spacer peptide to connect the α-subunit to the β-subunit.

One aspect of the invention includes isolated feline thyrotropin β-subunit polypeptide (SEQ ID NO: 1). This sequence constitutes an embodiment of the feline thyrotropin β-subunit polypeptide, as it is secreted and found in vivo, without the signal sequence. Another aspect of the invention includes isolated feline thyrotropin β-subunit polypeptide that includes a signal sequence (SEQ ID NO: 2). The signal sequence is an N-terminal, hydrophobic sequence that marks the protein for translocation across the endoplasmic reticulum membrane. While the signal sequence is retained for some peptides to provide a permanent membrane anchor, the signal sequences of thyrotropin subunits are cleaved, as they generally are for other secretory proteins, by a signal peptidase on the luminal side of the endoplasmic reticulum membrane. The signal sequence shown in SEQ ID NO: 2 is the sequence found in pituitary feline thyrotropin, and facilitates secretion in mammalian cells. However, other signal sequences may be used to enable secretion in other cell types. For example, a honey bee mellitin signal sequence may be used to facilitate secretion in insect cells. The polypeptide retaining the signal sequence is referred to herein as the prepeptide. The amino acid sequences of thyrotropin β-subunit polypeptide and prepeptide are diagrammed in FIG. 1.

Another aspect of the invention includes isolated feline thyrotropin α-subunit polypeptide (SEQ ID NO: 3). The α-subunit of feline thyrotropin may associate with a β-subunit in follicle stimulating hormone (FSH) and luteinizing hormone (LH), in addition to associating with the feline thyrotropin β-subunit. While SEQ ID NO: 3 shows an amino acid without a signal sequence, another aspect of the invention includes isolated feline thyrotropin β-subunit that still includes a signal sequence (SEQ ID NO: 4); namely, the prepeptide. The signal sequence, as noted above, is used to attach the polypeptide to endoplasmic reticulum membrane, and to aid in export of the protein from the cell. Signal sequences may be varied to suit the cell type chosen for protein expression, as known to those skilled in the art. The amino acid sequences of thyrotropin α-subunit polypeptide and prepeptide are diagrammed in FIG. 2. Note that the expressed polypeptide originally has a FLAG tag site and Factor Xa cleavage site. This is provided to aid in purification of the subunit, and is removed by cleavage at the Factor Xa cleavage site to provide the a-subunit itself. A wide variety of other tag and cleavage sequences are suitable for use in the invention, as known to those skilled in the art.

The invention also includes feline thyrotropin β-subunit polypeptide and feline thyrotropin α-subunit that are "yoked" together, for example, by a C-terminal peptide of human chorionic gonadotropin to form feline thyrotropin yoked polypeptide (SEQ ID NO: 5). A "yoked" polypeptide is essentially a form of fusion protein in which both subunits are expressed as part of one longer amino acid sequence, with a linker or spacer polypeptide that is preferably flexible, expressed between the two subunits that tethers or connects the two subunits together while allowing them to maintain their tertiary structure with relatively little interference from the spacer peptide. The spacer polypeptide of the feline thyrotropin yoked polypeptide (SEQ ID NO: 5) shown in FIG. 3 is a C-terminal peptide from human chorionic gonadotropin. However, the invention is not limited to the use of this spacer peptide for the formation of a feline thyrotropin yoked polypeptide. While the tandem order of subunits from 5' to 3' is β-subunit-CTP-α-subunit for SEQ ID NO: 5 and SEQ ID NO: 6, and this order is preferred, the invention also includes subunits provided in the reverse order with the α-subunit near the 5' end. The preparation of a feline thyrotropin yoked polypeptide is described in Example 3. A prepeptide version of the yoked feline thyrotropin is also provided (SEQ ID NO: 6). The technique of using spacer polypeptides to form yoked polypeptides is described by Grossman et al., J. Biol. Chem., 272, 21312 (1997).

Yoked (also called tethered) analogs of human thyrotropin (hTSH) and human chorionic gonadotropin (hCG) have been constructed with the C-terminus of the β subunit fused using a yoking peptide to the N-terminus of the α-subunit. The approach has allowed more extensive structure-function studies and also has resulted in generation of hormones with increased stability and activity. Grossmann et al., showed that the genetic fusion of hTSH α- and β-subunits using the carboxy-terminal peptide of the hCG β-subunit as a linker created a yoked form of hTSH whose receptor binding and bioactivity were comparable to native hTSH, but had higher thermostability and a longer plasma half-life. The yoked and dimeric hCG expressed in insect cells have been shown to have higher affinity for the LH/CG receptor than native urinary hCG, but are less potent in signal transduction (See Narayan et al., Mol. Endocrinol. 9, 1720 (1995)). The tandem order of subunits—β-subunit-CTP-αsubunit—was chosen based on the studies suggesting the importance of the N-terminal region of hCGβ and C-terminal region of the α-subunit in receptor binding and activation, as described by Ben-Menahem et al., J. Biol. Chem. 276, 29871 (2001). Fundamentally, this approach also ensures equimolar expression of the subunits and simultaneous affinity labeling of a single recombinant peptide rather than a heterodimer.

While the C-terminal peptide from human chorionic gonadotropin can be used to provide a suitable spacer polypeptide, a variety of polypeptides can be utilized to create a feline thyrotropin yoked polypeptide, so long as they satisfy the functional requirements of connecting the polypeptide subunits, preferably in a flexible fashion, while not interfering with the proper folding of the alpha and beta subunits. Preferably, the spacer polypeptide provides these functions while also providing a biologically active polypeptide with a longer plasma half-life. In this aspect of the invention, feline thyrotropin yoked polypeptide is a fusion protein in which the α-subunit is connected to the β-subunit using any of a variety of possible spacer peptides.

As used herein, the term "polypeptide" refers broadly to a polymer of two or more amino acids joined together by peptide bonds. The term "polypeptide" also includes molecules that contain more than one polypeptide joined by a disulfide bond, or complexes of polypeptides that are joined together, covalently or noncovalently, as multimers (e.g., dimers, tetramers). Thus, the terms peptide, oligopeptide, and protein are all included within the definition of polypeptide and these terms are used interchangeably. It should be understood that these terms do not connote a specific length of a polymer of amino acids, nor are they intended to imply or distinguish whether the polypeptide is produced using recombinant techniques, chemical or enzymatic synthesis, or is naturally occurring.

Substitutes for an amino acid in the polypeptides of the invention are preferably conservative substitutions, which are selected from other members of the class to which the amino acid belongs. For example, it is well-known in the art of protein biochemistry that an amino acid belonging to a grouping of amino acids having a particular size or characteristic (such as charge, hydrophobicity and hydrophilicity) can generally be substituted for another amino acid without substantially altering the structure of a polypeptide. For example, nonpolar (hydrophobic) amino acids include alanine, leucine, isoleucine, valine, proline, phenylalanine, tryptophan, and tyrosine. Polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Examples of preferred conservative substitutions include Lys for Arg and vice versa to maintain a positive charge; Glu for Asp and vice versa to maintain a negative charge; Ser for Thr so that a free —OH is maintained; and Gln for Asn to maintain a free $NH_2$.

Other amino acids and derivatives thereof that can be used include 3-hydroxyproline, 4-hydroxyproline, homocysteine, 2-aminoadipic acid, 2-aminopimelic acid, γ-carboxyglutamic acid, β-carboxyaspartic acid, ornithine, homoarginine, N-methyl lysine, dimethyl lysine, trimethyl lysine, 2,3-diaminopropionic acid, 2,4-diaminobutyric acid, homoarginine, sarcosine, hydroxylysine, substituted phenylalanines, norleucine, norvaline, 2-aminooctanoic acid, 2-aminoheptanoic acid, statine, β-valine, naphthylalanines, substituted phenylalanines, tetrahydroisoquinoline-3-carboxylic acid, and halogenated tyrosines.

Feline thyrotropin of the present invention, in its various yoked and heterodimeric forms, as well as its alpha and beta subunits, can tolerate a certain degree of variation in its amino acid sequence without significant disruption of its bioactivity. The term "feline thyrotropin" and the terms used to represent its various subunits and quaternary structures, as used herein, thus presume a certain allowed variation in structure, unless specifically restricted to a particular sequence. This variation includes substitution of one amino acid with another, as described, and also includes peptidometics in which one or more peptide linkages have been replaced with linkages such as —$CH_2NH$—, —$CH_2S$—, —$CH_2$—$CH_2$—, —CH=CH— (cis and trans), —$COCH_2$—, —CH(OH) $CH_2$—, and —$CH_2SO$—, prepared by methods known in the art. Preferred variants of feline thyrotropin or any of its constituent peptides include those sequences that are at least 80% identical, more preferably at least 90% identical, even more preferably at least 95% identical, and most preferably at least 99% identical to feline thyrotropin or its constituent peptides. Preferred variants of feline thyrotropin alpha or beta subunits also include those sequences that are 80% identical, more preferably at least 90% identical, even more preferably at least 95% identical, and most preferably at least 99% identical to feline thyrotropin alpha or beta subunits. Such variants contain one or more amino acid deletions, insertions, and/or substitutions relative to feline thyrotropin or its subunits, and may further include chemical and/or enzymatic modifications and/or derivatizations. Percent identity can be determined by a BLAST analysis.

Percent identity between two polypeptide sequences is generally determined by aligning the residues of the two amino acid sequences to optimize the number of identical amino acids along the lengths of their sequences; gaps in either or both sequences are permitted in making the alignment in order to optimize the number of identical amino acids, although the amino acids in each sequence must nonetheless remain in their proper order. Preferably, two amino acid sequences are compared using the Blastp program, version 2.2.10, of the BLAST 2 search algorithm, as described by Tatusova et al. (FEMS Microbiol. Lett., 174, 247-250 (1999)), and available on the world wide web at the National Center for Biotechnology Information website, under BLAST in the Molecular Database section. Preferably, the default values for all BLAST 2 search parameters are used, including matrix=BLOSUM62; open gap penalty=11, extension gap penalty=1, gap x_dropoff=50, expect=10, wordsize=3, and optionally, filter on. In the comparison of two amino acid sequences using the BLAST search algorithm, structural similarity is referred to as "identity."

Feline thyrotropin polypeptides of the invention can be produced on a small or large scale through use of numerous expression systems that include, but are not limited to, cells or microorganisms that are transformed with a recombinant vector into which a polynucleotide of the invention has been inserted. Such recombinant vectors and methods for their use are described below. These vectors can be used to transform a variety of organisms. Examples of such organisms include bacteria (for example, *E. coli* or *B. subtilis*); yeast (for example, *Saccharomyces* and *Pichia*); insects (for example, *Spodoptera*); plants; or mammalian cells (for example, COS, CHO, BHK, 293, VERO, HeLa, HEK, MDCK, W138, and NIH 3T3 cells). Also useful as host cells are primary or secondary cells obtained directly from a mammal that are transfected with a vector.

Synthetic methods may also be used to produce polypeptides and polypeptide subunits of the invention. Such methods are known and have been reported, Olson et al., Peptides, 9, 301, 307 (1988)). The solid phase peptide synthetic method is an established and widely used method, which is described in the following references: Stewart et al., Solid Phase Peptide Synthesis, W.H. Freeman Co., San Francisco (1969); Merrifield, J. Am. Chem. Soc., 85 2149 (1963); Meienhofer in "Hormonal Proteins and Peptides," ed.; C. H. Li, Vol. 2 (Academic Press, 1973), pp. 48-267; Barany and Merrifield, "The Peptides," eds. E. Gross and F. Meienhofer, Vol. 2 (Academic Press, 1980) pp. 3-285; and Clark-Lewis et al., Meth. Enzymol., 287, 233 (1997). Polypeptides can be readily purified by fractionation on immunoaffinity or ion-exchange columns; ethanol precipitation; reverse phase HPLC; chromatography on silica or on an anion-exchange resin such as DEAE; chromatofocusing; SDS-PAGE; ammonium sulfate precipitation; gel filtration using, for example, Sephadex G-75; ligand affinity chromatography, and the like. Polypeptides can also be readily purified through binding of a fusion polypeptide to separation media, followed by cleavage of the fusion polypeptide to release a purified polypeptide. For example, a fusion polypeptide that includes a factor Xa cleavage site between the polypeptide and an affinity tag polypeptide can be created. The fusion polypeptide can be bound to an affinity column to which the affinity tag polypeptide portion of the fusion polypeptide binds. The fusion polypeptide can then be cleaved with factor Xa to release the polypeptide. For example, such a system has been used in conjunction with a factor Xa removal kit using a FLAG affinity tag for purification of the polypeptides of the invention.

The invention includes methods of using feline thyrotropin polypeptide as immunogens or as immunoassay standards. The feline thyrotropin polypeptides useful in these roles include feline thyrotropin heterodimer, feline thyrotropin yoked polypeptide, feline thyrotropin β-subunit, and feline thyrotropin α-subunit. The present invention also includes these immunogens or immunoassay standards as prepared by the method of preparing polypeptide using transformed cell lines, as described in more detail below, as the antigenicity of the polypeptides may vary based on the cell line used and other aspects involved in their preparation. When used as immunogens, the feline thyrotropin polypeptides are used as a template for generating antibodies that specifically bind to one or more epitopes present on the polypeptides used as immunogens. When used as immunoassay standards, the feline thyrotropin polypeptides provide a reference level of polypeptide that can be used to evaluate the concentration of feline thyrotropin present in a solution based on binding by a particular antibody that specifically binds to the feline thyrotropin.

The invention also provides polynucleotides that encode the polypeptides of the invention. The term "polynucleotide" refers broadly to a polymer of two or more nucleotides covalently linked in a 5' to 3' orientation. The terms nucleic acid, nucleic acid sequence, and oligonucleotide are included within the definition of polynucleotide and these terms may be used interchangeably. It should be understood that these terms do not connote a specific length of a polymer of nucleotides, nor are they intended to imply or distinguish whether the polynucleotide is produced using recombinant techniques, chemical or enzymatic synthesis, or is naturally occurring. The polynucleotides of the invention can be DNA, RNA, or a combination thereof, and can include any combination of naturally occurring, chemically modified or enzymatically modified nucleotides.

Polynucleotides can be single-stranded or double-stranded, and the sequence of the second, complementary strand is dictated by the sequence of the first strand. The term "polynucleotide" is therefore to be broadly interpreted as encompassing a single stranded nucleic acid polymer, its complement, and the duplex formed thereby. "Complementarity" of polynucleotides refers to the ability of two single-stranded polynucleotides to base pair with each other, in which an adenine on one polynucleotide will base pair with a thymidine (or uracil, in the case of RNA) on the other, and a cytidine on one polynucleotide will base pair with a guanine on the other. Two polynucleotides are complementary to each other when a nucleotide sequence in one polynucleotide can base pair with a nucleotide sequence in a second polynucleotide. For instance, 5'-ATGC and 5'-GCAT are fully complementary, as are 5'-GCTA and 5'-TAGC.

Preferred polynucleotides of the invention include polynucleotides having a nucleotide sequence that is "substantially complementary" to (a) a nucleotide sequence that encodes a novel feline thyrotropin polypeptide according to the invention, or (b) the complement of such nucleotide sequence. "Substantially complementary" polynucleotides can include at least one base pair mismatch, such that at least one nucleotide present on a second polynucleotide, however the two polynucleotides will still have the capacity to hybridize. For instance, the middle nucleotide of each of the two DNA molecules 5'-AGCAAATAT and 5'-ATATATGCT will not base pair, but these two polynucleotides are nonetheless substantially complementary as defined herein. Two polynucleotides are substantially complementary if they hybridize under hybridization conditions exemplified by 2×SSC (SSC: 150 mM NaCl, 15 mM trisodium citrate, pH 7.6) at 55° C. Substantially complementary polynucleotides for purposes of the present invention preferably share at least one region of at least 20 nucleotides in length which shared region has at least 60% nucleotide identity, preferably at least 80% nucleotide identity, more preferably at least 90% nucleotide identity and most preferably at least 95% nucleotide identity. Particularly preferred substantially complementary polynucleotides share a plurality of such regions.

Nucleotide sequences are preferably compared using the Blastn program, version 2.2.10, of the BLAST 2 search algorithm, also as described by Tatusova et al. (FEMS Microbiol. Lett, 174, 247-250 (1999)), and available on the world wide web at the National Center for Biotechnology Information website, under BLAST in the Molecular Database section. Preferably, the default values for all BLAST 2 search parameters are used, including reward for match=1, penalty for mismatch=−2, open gap penalty=5, extension gap penalty=2, gap x_dropoff=50, expect=10, wordsize=11, and optionally, filter on. Locations and levels of nucleotide sequence identity between two nucleotide sequences can also be readily determined using CLUSTALW multiple sequence alignment software (J. Thompson et al., Nucl. Acids Res., 22:4673-4680 (1994)), available at from the world wide web at the European Bioinformatics Institute website in the "Toolbox" section as the ClustalW program.

It should be understood that a polynucleotide that encodes feline thyrotropin polypeptide according to the invention is not limited to a polynucleotide that contains all or a portion of naturally occurring genomic or cDNA nucleotide sequence, but also includes the class of polynucleotides that encode such polypeptides as a result of the degeneracy of the genetic code. The class of nucleotide sequences that encode a selected polypeptide sequence is large but finite, and the nucleotide sequence of each member of the class can be readily determined by one skilled in the art by reference to the standard genetic code, wherein different nucleotide triplets (codons) are known to encode the same amino acid. Likewise, a polynucleotide of the invention that encodes a variant or subunit of a feline thyrotropin polypeptide includes the multiple members of the class of polynucleotides that encode the selected polypeptide sequence.

One aspect of the present invention provides an isolated polynucleotide that encodes the feline thyrotropin β-subunit polypeptide, as shown in FIG. 1 as SEQ ID NO: 7. FIG. 1 also shows a preferred polynucleotide encoding thyrotropin β-subunit polypeptide (SEQ ID NO: 8) that contains an intron sequence. Note that a polynucleotide that "encodes" a polypeptide of the invention optionally includes both coding and noncoding regions, and it should therefore be understood that, unless expressly stated to the contrary, a polynucleotide that "encodes" a polypeptide is not structurally limited to nucleotide sequences that encode a polypeptide but can include other nucleotide sequences outside (i.e., 5' or 3' to) the coding region. Inclusion of an intron sequence, as in SEQ ID NO: 8, is preferred as it results in enhanced expression in mammalian cells.

Another aspect of the present invention provides an isolated polynucleotide that encodes the feline thyrotropin α-subunit polypeptide, as shown in FIG. 2 as SEQ ID NO: 9. SEQ ID NO: 10 provides an additional isolated polynucleotide that encodes the feline thyrotropin α-subunit, and further includes 98 additional bases upstream of the nucleotides encoding the signal sequence. These nucleotide sequences do not appear to be expressed as polypeptide, but their presence enhances transcription of the feline α-subunit polypeptide, providing an improved expression construct.

Examples describing the cloning and sequencing of feline thyrotropin α-subunit and the feline thyrotropin β-subunit are provided in Examples 1 and 2, below. Briefly, the feline thyroropin alpha and beta subunits were amplified by reverse transcriptase polymerase chain reaction (RT-PCR) from feline pituitary RNA or white blood cells, respectively. After isolating genomic DNA, primers were designed using consensus sequences of the thyrotropin subunits from various species, and thyrotropin was amplified along with the appropriate signal peptide.

The invention also includes an isolated polynucleotide that encodes the feline thyrotropin yoked polypeptide, as shown in FIG. 3 as SEQ ID NO: 11. The preparation of this polynucleotide is described in Example 3. Briefly, the nucleotide sequence encoding the full length alpha subunit, but excluding the signal sequence, was fused in frame with the chorionic gonadotropin CTP spacer polypeptide (SEQ ID NO: 13) to the 3' terminus of the beta subunit containing the coding sequence of the signal sequence and the secreted subunit using nucleases and ligases. The procedure to add the linker involves using primers that add approximately half of the linker to the 5' end of the alpha subunit and another which adds approximately half of the sequence to the 3'-end of the beta subunit. A restriction site is included on the 3' end of the beta piece and the 5' end of the alpha-FLAG piece and a three piece (beta, alpha-FLAG, cut vector) ligation is performed to obtain the final construct in the vector. FIG. 3 also shows a polynucleotide that encodes a feline thyrotropin yoked polynucleotide in which the β-subunit lacks the intron sequence (SEQ ID NO: 12). While not specifically shown in the figures, the invention also includes polynucleotide sequences that would encode a thyrotropin yoked polypeptide with a spacer polypeptide other than chorionic gonadotropin CTP.

The invention also includes vectors that may be used to transfect or transduce polynucleotides capable of expressing feline thyrotropin polypeptides into host cells. Both expression vectors and cloning vectors are provided. Vectors may be viral or nonviral, and may result in integration or non-integration of the polynucleotide. A vector may include, but is not limited to, any plasmid, phagemid, F-factor, virus, cosmid, or phage. The vector may be in a double or single stranded linear or circular form. The vector can also transform a prokaryotic or eukaryotic host either by integration into the cellular genome or exist extrachromosomally (e.g. autonomous replicating plasmid with an origin of replication).

The polynucleotide in the vector can be under the control of, and operably linked to, an appropriate promoter or other regulatory sequence for transcription in vitro or in a host cell, such as a eukaryotic cell, or a microbe, e.g. bacteria. A regulatory sequence refers to nucleotide sequences located upstream (5' non-coding sequences), within, or downstream (3' non-coding sequences) of a coding sequence, and which influence the transcription, RNA processing or stability, or translation of the associated coding sequence. Examples of regulatory sequences include enhancers, promoters, translation leader sequences, introns, and polyadenylation signal sequences. They include natural and synthetic sequences as well as sequences that may be a combination of synthetic and natural sequences. Regulatory sequences are not limited to promoters. However, some suitable regulatory sequences useful in the present invention will include, but are not limited to, constitutive promoters, tissue-specific promoters, development-specific promoters, inducible promoters and viral promoters. Inclusion of bases upstream from the thyrotropin polypeptides in the natural source may be included along with the bases responsible for expression of polypeptide amino acids. For example, inclusion of 98 upstream bases for the polynucleotide encoding feline thyrotropin α-subunit polypeptide of SEQ ID NO: 10 obtained by amplification of feline pituitary RNA results in enhanced expression of the polypeptide, thus providing an improved expression construct. Interestingly, the START codon directly precedes the signal sequence in SEQ ID NO: 10, indicating it is likely that the signal sequence represents additional sequence in the synthesized pre- or pro-hormone form that is cleaved prior to secretion from the pituicyte or cell in vitro.

An example of an expression vector that may be used in the present invention is shown in FIG. 4, which shows expression vector for feline thyrotropin yoked polypeptide. This expression vector has an EF1-α (elongation factor 1-α) promoter upstream of the polynucleotide sequence used to express feline thyrotropin yoked polypeptide. The expression vector also has a puromycin resistance gene that allows for selection of transformed cells. The polynucleotide capable of expressing feline thyrotropin yoked polypeptide has a restriction site at each end (Eco RI and Not 1), a signal sequence (SS), a strand encoding the β-subunit, a strand encoding the CTP spacer, a strand encoding the α-subunit, and finally a strand encoding FLAG that may be used for affinity purification of the expressed polypeptide.

Methods to introduce a polynucleotide into a vector are well known in the art (Sambrook et al., Molecular Cloning: A Laboratory Manual, 3rd edition, Cold Spring Harbor Press, Cold Spring Harbor, N.Y. (2001)). Briefly, a vector into which a polynucleotide is to be inserted is treated with one or more restriction enzymes (restriction endonuclease) to produce a linearized vector having a blunt end, a "sticky" end with a 5' or a 3' overhang, or any combination of the above. The vector may also be treated with a restriction enzyme and subsequently treated with another modifying enzyme, such as a polymerase, an exonuclease, a phosphatase or a kinase, to create a linearized vector that has characteristics useful for ligation of a polynucleotide into the vector. The polynucleotide that is to be inserted into the vector is treated with one or more restriction enzymes to create a linearized segment having a blunt end, a "sticky" end with a 5' or a 3' overhang, or any combination of the above. The polynucleotide may also be treated with a restriction enzyme and subsequently treated with another DNA modifying enzyme. Such DNA modifying enzymes include, but are not limited to, polymerase, exonuclease, phosphatase or a kinase, to create a polynucleotide that has characteristics useful for ligation of a polynucleotide into the vector.

The treated vector and polynucleotide are then ligated together to form a construct containing a polynucleotide according to methods known in the art (Sambrook et al., Molecular Cloning: A Laboratory Manual, 3rd edition, Cold Spring Harbor Press, Cold Spring Harbor, N.Y. (2001)). Briefly, the treated nucleic acid fragment and the treated vector are combined in the presence of a suitable buffer and ligase. The mixture is then incubated under appropriate conditions to allow the ligase to ligate the nucleic acid fragment into the vector.

In the case of a polypeptide or polynucleotide that is naturally occurring, it is preferred that such polypeptide or polynucleotide be isolated and, optionally, purified. An "isolated" polypeptide or polynucleotide is one that is separate and discrete from its natural environment. A "purified" polypeptide or polynucleotide is one that is at least 60% free, preferably 75% free, and most preferably 90% free from other components with which they are naturally associated. Polypeptides and nucleotides that are produced outside the organism in which they naturally occur, e.g., through chemical or recombinant means, are considered to be isolated and purified by definition, since they were never present in a natural environment.

The invention includes antibodies that specifically bind to feline thyrotropin. Antibodies may be developed that specifically bind to feline thyrotropin heterodimer, feline thyrotropin yoked polypeptide, the feline thyrotropin alpha and beta subunit polypeptides, and any other combinations or fragments of feline thyrotropin polypeptide. As used herein, the phrase "specifically binds" and other permutations of the phrase refers to an antibody or other compound that will, under appropriate conditions, interact with a specific molecule even in the presence of a diversity of potential binding targets. With respect to an antibody, "specifically binds" means the antibody interacts only with the epitope of the antigen that induced the synthesis of the antibody, or interacts with a structurally related epitope.

Accordingly, feline thyrotropin and constituent peptides as described herein and any portion thereof can be used as antigens to produce antibodies, including vertebrate antibodies, hybrid antibodies, chimeric antibodies, humanized antibodies, altered antibodies, univalent antibodies, monoclonal and polyclonal antibodies, Fab proteins and single domain antibodies. If the polypeptides are not sufficiently immunogenic, they can be modified by covalently linking them to an immunogenic carrier, such as keyhole limpet hemocyanin (KLH), bovine serum albumin, ovalbumin, mouse serum albumin, rabbit serum albumin, and the like.

If polyclonal antibodies are desired, a selected animal (e.g., mouse, rabbit, goat, horse or bird, such as chicken) is immunized with the desired antigen. Serum from the immunized animal is collected and treated according to known procedures. If serum containing polyclonal antibodies to a feline thyrotropin heterodimer, yoked polypeptide, or its subunits contains antibodies to other antigens, the polyclonal antibodies can be purified by immunoaffinity chromatography. Techniques for producing and processing polyclonal antisera are known in the art (see for example, Mayer and Walker eds. Immunochemical Methods in Cell and Molecular Biology (Academic Press, London) (1987), Coligan, et al., Unit 9, Current Protocols in Immunology, Wiley Interscience (1991), Green et al., Production of Polyclonal Antisera, in Immunochemical Protocols (Manson, ed.), pages 1-5 (Humana Press 1992); Coligan et al., Production of Polyclonal Antisera in Rabbits, Rats, Mice and Hamsters, in Current Protocols in Immunology, section 2.4.1 (1992)).

Monoclonal antibodies directed against the feline thyrotropin polypeptides are included in the invention, and can be readily produced by one skilled in the art. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus (See Monoclonal Antibody Production. Committee on Methods of Producing Monoclonal Antibodies, Institute for Laboratory Animal Research, National Research Council; The National Academies Press; (1999), Kohler & Milstein, Nature, 256: 495 (1975); Coligan et al., sections 2.5.1-2.6.7; and Harlow et al., Antibodies: A Laboratory Manual, page 726 (Cold Spring Harbor Pub. 1988)). Panels of monoclonal antibodies produced against the polypeptides of the invention can be screened for various properties, for example epitope affinity. For a detailed example of monoclonal antibody preparation, see Example 7 below.

Antibodies can also be prepared through use of phage display techniques. Phage display methods to isolate antigens and antibodies are known in the art and have been described (Gram et al., Proc. Natl. Acad. Sci., 89:3576 (1992); Kay et al., Phage display of peptides and proteins: A laboratory manual. San Diego: Academic Press (1996); Kermani et al., Hybrid, 14:323 (1995); Schmitz et al., Placenta, 21 Suppl. A:S106 (2000); Sanna et al., Proc. Natl. Acad. Sci., 92:6439 (1995)).

An antibody of the invention may also be a "humanized" monoclonal antibody. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described (Orlandi et al., Proc. Nat'l Acad. Sci. USA, 86:3833 (1989) which is hereby incorporated in its entirety by reference). Techniques for producing humanized monoclonal antibodies are described (Jones et al., Nature, 321:522 (1986); Riechmann et al., Nature, 332:323 (1988); Verhoeyen et al, Science, 239:1534 (1988); Carter et al., Proc. Nat'l Acad. Sci. USA, 89:4285 (1992); Sandhu, Crit. Rev. Biotech., 12:437 (1992); and Singerct C., J. Immunol., 150:2844 (1993)).

In addition, antibodies of the present invention may be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens, and the mice can be used to produce human antibody-secreting hybridomas. Methods for obtaining human antibodies from transgenic mice are described (Green et al., Nature Genet., 7:13 (1994); Lonberg et al., Nature, 368:856 (1994); and Taylor et al., Int. Immunol., 6:579 (1994)).

Antibody fragments of the invention can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described (U.S. Pat. Nos. 4,036,945; 4,331,647; and 6,342,221, and references contained therein; Porter, Biochem. J., 73:119 (1959); and Coligan et al. at sections 2.8.1-2.8.10 and 2.10.1-2.10.4).

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Antibodies to feline thyrotropin polypeptide can be screened, in accordance with the invention, to determine the identity of the epitope to which they bind. An epitope refers to the site on an antigen, such as a polypeptide of the invention, to which the paratope of an antibody binds. An epitope usually consists of chemically active surface groupings of molecules, such as amino acids or sugar side chains, and can have specific three-dimensional structural characteristics, as well as specific charge characteristics. Methods which can be used to identify an epitope are known in the art (Harlow et al., Antibodies: A Laboratory Manual, page 319 (Cold Spring Harbor Pub. 1988).

Characterization of specific binding of anti-feline thyrotropin antibodies is particularly relevant in light of the fact that feline thyrotropin, like many other pituitary glycoproteins, displays extensive polymorphism and changes in bioactivity which may be influenced by endocrine status. Various isoforms are secreted which differ in glycosylation pattern, bioactivity and circulatory halflife. Ultrasensitive immunoassays for pituitary glycoproteins have been able to reveal that the glycosylation pattern of plasma hormones is different from that of pituitary stock and varies as per the pathophysiology of pituitary axis (Zerfaoui, M, Ronin C., Europ. J. Clin. Chem and Clin. Biochem., 34, 749 (1996). Discrepancies in immunoassays in detection of glycoproteins has been noticed when polyclonal antibodies were used in the assay as the antibodies raised against pituitary hormone do not necessarily uniformly recognize circulating isoforms. A recent study that compared the recognition of pituitary and recombinant human thyrotropin by various polyclonal and monoclonal antibodies before and after neuraminidase treatment showed that removal of sialic acid abolished the binding of pituitary human thyrotropin to anti-β monoclonal antibodies. Thus, to measure all forms of the hormone, antibodies may optionally be used that bind to epitopes that are glycosylation independent.

The invention provides methods to detect physiological levels of feline thyrotropin in a sample. Briefly, this method involves obtaining a sample, typically from a cat, contacting the sample with anti-feline thyrotropin antibody, and then assessing the formation of a complex between the antibody and any feline thyrotropin that may be present in the sample. In a preferred embodiment, the diagnostic method of the invention is an immunoassay. Purified feline thyrotropin (as a heterodimer, yoked polypeptide, or alpha or beta subunit) is useful as a polypeptide standard in an immunoassay, and as an immunogen for preparing antibodies useful in the assay. The assay utilizes one or more antibodies induced against an epitope of any of these compounds in a competitive and non-competitive assay such as a radioimmunoassay, immunoenzymometric assay, immunofluorometric assay or enzymoimmunoassays assays, or in chemiluminescent methods with horseradish peroxidase or alkaline phosphatase or other chemiluminescent detection agents to analyze, for example, feline heterodimer concentrations in bodily fluids such as plasma, serum or urine. These assays can be used to measure the amount of circulating feline thyrotropin or its subunits in bodily fluids. In addition to immunoassays, polypeptide standards and antibodies may also be used for other analytical techniques such as western blotting and chromatographic analysis. See example 8 below for details on the immunological detection of feline thyrotropin proteins in a particular embodiment of the invention.

Sandwich-type immunoassays utilizing two antibodies against feline thyrotropin are a particularly preferred embodiment of the invention. Preferably, sandwich-type immunoassays of the invention utilizing monoclonal antibody against feline thyrotropin β-subunit and either monoclonal or polyclonal antibody against the feline thyrotropin α-subunit display sensitivities of about 0.1 μU/ml to 0.01 μU/ml. More preferably, the immunoassays of the invention display sensitivities of about 0.005 to 0.01 μU/ml. In sandwich assays, the antibody specific to the variable β-subunit may be attached to wells used in the immunoassay. Antibody specific for the α-subunit, provided with label, is then used to identify bound thyrotropin after washing of the wells. Use of antibody against the β-subunit within the well is preferred as this avoids binding by other hormones that utilize the α-subunit that could result in erroneous results. The specificity of antibody used to detect feline thyrotropin already bound within the well can be significantly lower. This second antibody should include a label to allow detection of bound thyrotropin. While monoclonal or polyclonal antibodies that specifically bind to the feline thyrotropin α-subunit are preferred for this role, antibodies against the β-subunit may be used, as well crossreactive antibodies such as crossreactive antibody against canine or ovine thyrotropin. The immunoassays using chemiluminescence as a label that can achieve a high specific activity with minimal change in immunoreactivity. The normal thyrotropin levels in animals range from 0.2-4 μU/ml. In clearly hyperthyroid subjects, thyrotropin is typically suppressed to levels below 0.005 μU/ml (0.0005 ng/ml).

The method of detecting feline thyrotropin may be used as a method of diagnosing a feline thyroid disorder. Disorders of the thyroid include autoimmune disorders, thyroiditis (inflammation or infection of the thyroid), and cancer, all of which can result in hypothyroidism or hyperthyroidism. A preferred embodiment of the invention used the method of detecting feline thyrotropin to diagnose feline hyperthyroidism, which as noted above is recognized as the most common endocrine disorder in cats. Feline, as used in the present invention, is merely the adjective form of cat, and refers to animals of the family Felidae. The preferred type of cats for use and treatment in the invention are cats of the genus *Felis*, with the domestic species *Felis catus* being particularly preferred.

Diagnosis, as defined herein, refers to the act or process of determining the nature and cause of a disease through examination of a patient or samples obtained from the patient. More particularly, diagnosis refers to the implementation of methods for in vitro detection of thyroid disease or disorders, such as those mentioned above, associated with the presence or absence in the patient of feline thyrotropin hormone and its analogs and subunits, capable of being involved directly or indirectly in the process of the appearance and/or development of these diseases, and of being recognized by the anti-feline thyrotropin antibodies of the invention.

Diagnosis may involve an immunoassay to determine the total amount of feline thyrotropin and its analogs and subunits. For feline hyperthyroidism, feline thyrotropin suppression occurs due to negative feedback from excessive quantities of triiodothyronine ($T_3$) and thyroxine ($T_4$). A sensitive assay is thus preferred for diagnosis of feline thyrotropin, as the levels of feline thyrotropin in cats with hyperthyroidism will be typically be lower than normal. For other diagnostic applications, such as monitoring the success of treatment with antithyroid drugs, a less sensitive assay may be used. Detection of feline thyrotropin levels may also be used to assess the predisposition of a cat to other problems associated with unusual thyrotropin levels.

The invention also includes methods of treating a mammal suspected of having hyperthyroidism by administering to the mammal an appropriate amount of feline thyrotropin heterodimer. Treatment with the heterodimer including the alpha and beta subunits or the yoked polypeptide is preferred as these are the active forms of feline thyrotropin. The α-subunit and the β-subunit show little or no activity when used in isolation.

Treatment of cats using feline thyrotropin is preferred. Treatment of feline hyperthyroidism must be adjusted in response to the clinical presentation of the cat. Because every animal reacts differently to a given dose of feline thyrotropin, the thyrotropin treatment needs to be adjusted to the individual's needs with regard to dose of thyrotropin and frequency of administration. Stimulation of feline thyroid glandular function by intravenously administered TSH with dosages ranging from 0.1-1 U/kg are preferred, with doses as low as 10 µg per animal being effective (See Hoenig, M. and Ferguson, D. C., Amer. J. Vet. Res. 44:1229-1232, (1983)). Although heterodimeric feline TSH has been shown to have biological activity in vitro on TSH receptor signal transduction, the activity in vivo appears to depend not only on receptor affinity but also on the rate of metabolic degradation. Therefore, appropriate glycosylation pattern and even bioengineering of the structure of feline TSH, such as yoking the two subunits, may serve to increase the net biological activity in the whole animal.

A preferred embodiment of the method of treating feline hyperthyroidism involves the use of feline thyrotropin, as a heterodimer or yoked polypeptide, as a thyroid radiosensitizing agent. Feline thyrotropin in this role acts to stimulate activity of the thyroid, which in turn renders the thyroid more susceptible to ablation by radioiodide. As feline hyperthyroidism generally involves overactivity of the thyroid, often due to the presence of a thyroid adenoma, thyroid ablation is an effective form of therapy.

Radioiodide treatment has been highly effective in treating the generally benign hyperfunctional thyroid adenomas seen in the vast majority of cats. Most radiation therapists now opt for a single dose of 3-4 mCi of radioiodide for treatment, and a single dose is effective in over 90% of cases. At this dosage, the induction of permanent hypothyroidism is rare. Despite the apparent success of this treatment, radioiodide which IS NOT taken up by the thyroid tissue creates a significant hazard for hospital personnel and animals are hospitalized for generally at least 7 days to reduce the hazard to the owners. Cats differ from people for radioiodide treatment in that the radioactivity concentrated to their salivary glands can be transferred to the haircoat in the process of the cat's grooming process.

A factor not often considered in the efficacy of ablative radioiodide is that when a tracer dose is used to calculate an ablative dose, the resulting value may range 10-fold from 1 to 10 mCi. See Broome et al., Am J. Vet. Res., 49(2), 193 (1988). Part of this variation may occur because of the considerable variation in radioiodine uptake caused by the widely varying, but generally high, iodide content of cat foods. Studies of thyroid cell lines from cats have demonstrated that, despite apparent autonomy of function, TSH can increase cyclic AMP and iodide uptake in hyperthyroid cells. See Studer et al., Endocrine Rev 10 (2), 125. In the hyperthyroid cat, TSH is predicted to be suppressed or normal if antithyroid drugs are being used, so the stimulatory effect for radioiodide uptake would be lost. Recombinant feline TSH may be used to safely overcome some of these variations. Further, by reducing the necessary radioactivity dosage and cost, and reducing the whole body radiation exposure, less isotope will be lost rapidly to the saliva, gastrointestinal secretions and urine, reducing the radiation exposure to hospital personnel and clients. Administration of TSH will typically increase thyroid uptake by as much as 2-3 fold.

In human studies, doses as low as 10 µg (~0.14 µg/kg) of recombinant human TSH (rhTSH) increased the radioactive iodide uptake (RAIU) to 1.67-fold with a dose of 30 µg (~0.43 µg/kg) increasing it by almost 2-fold. In another study, a higher dose (900 µg; ~13 µg/kg) did not increase radioiodide uptake further. Huysmans et al, J. Clin. Endocrin. & Metab., 85(10), 3592 (2000). Comparable levels (µg/kg) are expected to be effective in cats. However, as cats are often iodine-replete, a relatively high dose of about 1-3 µg/kg is preferred. Huysmans et al. also demonstrates that recombinant human TSH dramatically improves uptake by thyroid cancer metastastatic sites and reduces the dose of radiiodide seen by the rest of the body.

The invention also provides pharmaceutical compositions that can be used for the administration of feline thyrotropin polypeptides of the invention to a patient in need thereof, such as a feline. In one example, a pharmaceutical composition can contain a feline thyrotropin polypeptide, or analog thereof, and a pharmaceutically acceptable carrier. In another example, a pharmaceutical composition can contain an antibody that specifically binds feline thyrotropin of the invention, and a pharmaceutically acceptable carrier.

The pharmaceutical compositions of the invention may be prepared in many forms that include tablets, hard or soft gelatin capsules, aqueous solutions, suspensions, and liposomes and other slow-release formulations, such as shaped polymeric gels. An oral dosage form may be formulated such that the polypeptide or antibody is released into the intestine after passing through the stomach. Such formulations are described in U.S. Pat. No. 6,306,434 and in the references contained therein.

Oral liquid pharmaceutical compositions may be in the form of, for example, aqueous or oily suspensions, solutions, emulsions, syrups or elixirs, or may be presented as a dry product for constitution with water or other suitable vehicle before use. Such liquid pharmaceutical compositions may contain conventional additives such as suspending agents, emulsifying agents, non-aqueous vehicles (which may include edible oils), or preservatives.

The feline thyrotropin polypeptide or anti-feline thyrotropin antibody can be formulated for parenteral administration (e.g., by injection, for example, bolus injection or continuous infusion) and may be presented in unit dosage form in ampules, prefilled syringes, small volume infusion containers or multi-dose containers with an added preservative. The pharmaceutical compositions may take such forms as suspensions, solutions, or emulsions in oily or aqueous vehicles, and may contain formulatory agents such as suspending, stabilizing and/or dispersing agents. Pharmaceutical compositions suitable for rectal administration can be prepared as unit dose suppositories. Suitable carriers include saline solution and other materials commonly used in the art.

For administration by inhalation, feline thyrotropin polypeptide or anti-thyrotropin antibody can be conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, feline thyrotropin polypeptide or anti-thyrotropin antibody may take the form of a dry powder composition, for example, a powder mix of a modulator and a suitable powder base such as lactose or starch. The powder composition may be presented in unit dosage form in, for example, capsules or cartridges or, e.g., gelatin or blister packs from which the powder may be administered with the aid of an inhalator or insufflator. For intra-nasal administration, feline thyrotropin polypeptide or anti-thyrotropin antibody may be administered via a liquid spray, such as via a plastic bottle atomizer.

Feline thyrotropin polypeptide or anti-thyrotropin antibody can be formulated for transdermal administration. Feline thyrotropin polypeptide or anti-thyrotropin antibody can also be formulated as an aqueous solution, suspension or dispersion, an aqueous gel, a water-in-oil emulsion, or an oil-in-water emulsion. A transdermal formulation may also be prepared by encapsulation of a feline thyrotropin polypeptide or anti-thyrotropin antibody within a polymer, such as those described in U.S. Pat. No. 6,365,146. The dosage form may be applied directly to the skin as a lotion, cream, salve, or through use of a patch. Examples of patches that may be used for transdermal administration are described in U.S. Pat. Nos. 5,560,922 and 5,788,983.

It will be appreciated that the amount of feline thyrotropin polypeptide or anti-thyrotropin antibody required for use in treatment will vary not only with the particular carrier selected but also with the route of administration, the nature of the condition being treated and the age and condition of the patient. Ultimately the attendant health care provider may determine proper dosage. In addition, a pharmaceutical composition may be formulated as a single unit dosage form.

The invention further includes transgenic eukaryotic cells including feline thyrotropin-expressing polynucleotides. These cells represent the development of permanent cell lines that can be used to express feline thyrotropin heterodimer, feline thyrotropin yoked polypeptide, feline β-subunit polypeptide, and feline α-subunit polypeptide. Expression of feline thyrotropin constructs in three different cell systems is described in Example 5, below. While any suitable eukaryotic cell may be transformed by vectors containing nucleic acid sequences capable of expressing feline thyrotropin, cells that provide a level and pattern of glycosylation similar to that seen in mammalian cells are preferred. The choice of eukaryotic cell is significant, as different cells result in different glycosylation of the resulting expressed polypeptides, which as noted above may have a significant effect on the antigens present on the polypeptide. However, while glycosylation will vary depending on the cell line, feline thyrotropin polypeptide expressed from any eukaryotic cell line is expected to have at least some antigenic sites useful for detecting feline thyrotropin in vivo.

While mammalian cells are preferred, other eukaryotic cells may be suitable if they exhibit sufficient levels of protein glycosylation. One example of such cells is MIMIC™ insect cells. MIMIC™ cells have shown higher levels of polypeptide expression, with up to 10-20 µg/ml being recovered, but may also show more variable antigenicity. For secreted and membrane associated proteins, a signal peptide at the amino-terminus is responsible for targeting the polypeptide to the endoplasmic reticulum ER. The efficiency of secretion of the baculovirus system can be increased by using signal peptides of insect origin to direct the secretion of a foreign protein through the protein synthesis and secretary pathways. Insect cells infected with a baculovirus recombined with the gene encoding propapain fused to the sequence encoding the honeybee melittin signal peptide secreted over five times more papain precursor than the wild-type prepropapain which used the plant signal peptide (Tessier, et al., Gene, 98(2), 177 (1991)). Substitution of natural signal sequences with the signal sequences from honeybee mellitin promotes a high level of expression of a glycosylated form of gp120 and efficient secretion. However, use of honeybee melittin signal peptide does not ensure proper processing of recombinant proteins. The mature TSHβ, which has 118 amino acid residues and a 20 amino acid signal peptide, is encoded by the last two exons. Since the baculovirus expression system also recommends removal of the intron in the sequence for better expression in insect cells an overlap PCR was performed on the intron in the TSHβ and also substituted the mammalian signal sequence with the honeybee mellitin signal sequence. Preparation of constructs using the baculovirus expression system are described in Example 4.

Like other eukaryotic cells, insect cells modify proteins by N-glycosylation. The major processed N-glycan produced by insect cells is usually the paucimannosidic structure, Man3GlcNAc2-N-Asn. The N-glycosylation pathway was extended to insect cells as described in Examples 4 and 5. Genetically transformed insect cells with mammalian β1,4-galactosylatransferase and α2,6-sialyltransferase genes have been described (Hollister et al., Glycobiology v. 11, n .1, p. 1 (2001)). Stably transformed insect cells with β1,4-galactosyltransferase can be used as modified hosts for conventional baculovirus expression vectors to produce mammalianized glycoprotein glycans which more closely resemble those produced by higher eukaryotes. Mimic™ Sf9 Insect Cell line (Invitrogen, Carlsbad, Calif.), a derivative of the Sf9 insect cell line were modified to stably express a variety of mammalian glycosyltransferases. Typically, insect cells are unable to process N-glycans to the extent that mammalian cells do. The addition of mammalian glycosyltransferases like α2,6-sialyltransferase, β4-galactosyltransferase, N- acetylglucosaminyltransferase I and N-acetylglucosaminyltransferase II to the Mimic™ Sf9 Insect Cells allows for production of biantennary, terminally sialyated N-glycans from insect cells (Hollister, et al., Glycobiology, v. 13, n. 6, p. 487 (2003)).

Cells were transfected using vectors as described. In one embodiment, the vector shown in FIG. 4 may be used, which includes an EF-1α promoter and a puromycin gene to aid in selection of transformed cells. Transfection solution containing vector is added to cells, which are then allowed to grow in culture for several days. In particular embodiments, stable PEAK™ cell lines expressing both yoked thyrotropin and feline thyrotropin α-subunit were developed using a puromycin selection marker. In order to express feline thyrotropin α/β heterodimer, cells were cotransfected with both feline thyrotropin α-subunit and feline thyrotropin β-subunit in PEAK vectors. Expression levels of the heterodimer in PEAK cells was 1-1.5 µg/ml. Expression of fTSH was also carried out in Sf9 cells using the baculovirus vector. Preferably, vectors that lead to the stable expression of the desired feline thyrotropin polypeptides are used.

An embodiment of the invention also includes cells transformed with polynucleotides including nucleic acid sequences that express only the feline thyrotropin α-subunit. As noted above, the thyrotropin α-subunit is also used to form luteinizing hormone and follicle stimulating hormone, when combined with the appropriate β-subunit of these different glycoprotein hormones. A cell line that stably expresses feline thyrotropin α-subunit is thus a valuable resource for producing a variant of different hormones when the α-subunit is supplanted by further transformation of the cells with polynucleotides including nucleic acid sequences encoding the β-subunit of either follicle stimulating hormone or luteinizing hormone.

The invention also includes methods of making feline thyrotropin polypeptides by transfecting eukaryotic cells with a vector including a polynucleotide with a nucleotide sequence encoding feline thyrotropin polypeptide. The method may utilize a variety of suitable eukaryotic cells, with PEAK™ human embryonic kidney cells and MIMIC™ Sf9 cells being preferred. The method also may use any of the large variety of vectors disclosed in the discussion of vectors. Preferably, proteins prepared by this method are subsequently purified. One method of enabling the ready purification of expressed protein is to include an affinity tag, such as the FLAG epitope. Example 6 describes how recombinant feline thyrotropins were immunopurifed from expression media using ANTI- FLAG® M2 monoclonal antibody affinity gel. While use of the FLAG epitope represents one embodiment of the invention, various other means of purifying expressed feline thyrotropin will be readily apparent to those skilled in the art.

The method of making feline thyrotropin polypeptides includes methods of making feline thyrotropin heterodimer, feline thyrotropin yoked polypeptide, and both feline thyrotropin α-subunit and feline thyrotropin β-subunit. The invention also includes methods of making pituitary glycoprotein hormones using a cell line that permanently expresses feline thyrotropin α-subunit. When such a cell line is supplanted by further transformation of the cells with polynucleotides including nucleic acid sequences encoding the β-subunit of either follicle stimulating hormone or luteinizing hormone, follicle stimulating hormone or luteinizing hormone, respectively, may also be prepared.

Once feline thyrotropin polypeptides have been prepared, it may be desirable to test the prepared polypeptides for activity. This can be done using either in vitro or in vivo testing systems. An understanding of the biological effects of thyrotropin is important for devising appropriate testing systems for its bioactivity. For example, a close relationship exists between the binding of TSH to its receptor and the activation of adenylate cyclase. Many of the hormone's effects are mediated by cAMP. The cAMP cascade activation is enough to promote thyroid gland epithelial cell hyperplasia and even induce hyperthyroidism. For example, cAMP binds to 'cAMP' responsive element (CRE) on target genes like 3-hydroxy-3-methylglutaryl coenzyme reductase, whose transcription was significantly increased by TSH in FRTL-5 cells. Thyrotropin also stimulates hydrolysis of phosphatidylinositol-4,5-bisphosphate (PIP2) by phospholipase C and results in the formation diacylglycerol (DAG) and inositol-1, 4,5-triphosphate (IP3). IP3 mobilizes intracellular Ca2+, which activates Ca2+ and calmodulin-dependent protein kinase (Ca—CaM). DAG activates Ca2+-phospholipid-dependent protein kinase C (PKC). Both Ca—CAM kinase and PKC phosphorylate numerous proteins in the nucleus, plasma membrane and cytosol resulting in cell responses including hormone secretion and gene expression. Example 9 below utilizes this biochemistry to determine the biological activity of feline TSH constructs expressed in insect and mammalian cells using the JP09 cell line which is a CHO cell engineered to have the human TSH receptor expressed. In addition to providing useful testing methodologies, this example also demonstrates the biological activity of thyrotropin polypeptides prepared utilizing methods of the invention.

The invention provides kits that contain reagents used for diagnosing feline hyperthyroidism in a feline. Such kits can contain packaging material and an antibody that specifically binds to feline thyrotropin. Such kits may be used by medical personal for the formulation of pharmaceutical compositions that contain anti-thyrotropin antibody of the invention. The packaging material will provide a protected environment for the anti-thyrotropin antibody. For example, the packaging material may keep the anti-thyrotropin antibody from being contaminated. In addition, the packaging material may keep the anti-thyrotropin antibody in solution from becoming dry. Examples of suitable materials that can be used for packaging materials include glass, plastic, metal, and the like. Such materials may be silanized to avoid adhesion of the anti-thyrotropin antibody to the packaging material. The kit may optionally include additional components such as buffers, reaction vessels, secondary antibodies, and syringes The invention also encompasses various other types of kits that may be used to package useful reagents of the present invention. For example, different embodiments of the invention provide kits containing recombinant feline thyrotropin useful as an immunoassay standard, kits containing recombinant feline thyrotropin useful as immunogens, and feline thyrotropin for administration as a radiosensitizing agent to treat feline hyperthyroidism. While the bioactive forms of feline thyrotropin such as feline thyrotropin heterodimer and feline thyrotropin yoked polypeptide are preferred for use as radiosensitizing agents, these forms as well as the alpha and beta subunits are suitable for use as immunoassay standards or immunogens. All of these kits are provided with the packaging material needed to protect the reagent, and additional useful components such as buffers or reaction vessels, as described above.

EXAMPLES

The present invention is illustrated by the following examples. It is to be understood that the particular examples, materials, amounts, and procedures are to be interpreted broadly in accordance with the scope and spirit of the invention as set forth herein.

Example 1

Cloning and Sequencing of Feline TSH Alpha-Subunit

Cloning and sequencing of the α-subunit was carried out as follows. First, feline thyroropin α-subunit was amplified by RT-PCR from feline pituitary RNA. The first step here was RNA extraction from feline pituitary. RNaqueous kit was used for RNA extraction according to the protocol and buffers provided by the supplier (Ambion Inc, Austin, Tex.). In brief, the frozen tissue was ground under liquid nitrogen with 100 μl of lysis buffer. Another 100 μl of lysis buffer was added to the tissue and an equal volume of 64% ethanol was added, mixed gently and transferred to a filter cartridge provided by the suppler and centrifuged for 30-60 sec at 14000 rpm. After washing the filter cartridge twice, RNA was eluted using 40 μl of preheated elution solution. DNase buffer and DNase were added to the eluted RNA and incubated at 37° C. for 30 min followed by DNase inactivation reagent and ethanol precipitation of RNA.

In the next step, reverse transcriptase polymerase chain reaction was conducted. Primers previously used to amplify equine TSH were used to amplify the feline common α subunit using RT-PCR from pituitary RNA. The 24 amino acid leader sequence was also amplified along with the mature protein. Retroscript RT-PCR kit was used to generate cDNA following the protocol provided by the supplier (Ambion Inc, Austin, Tex.). The polymerase chain reaction was then used to amplify feline alpha-subunit, and addition of the Factor Xa cleavage site and the FLAG immunoaffinity tag on the 3' end was carried out. Primers were design from the consensus sequences of canine, equine and rat TSH and used to amplify the feline alpha-subunit. An immunoaffinity tag FLAG was included in the primer amplifying the 3' end of α-subunit. The FLAG octapeptide aided immunoaffinity purification and immunodetection by ANTI-FLAG® M2 monoclonal antibody (Sigma-Aldrich, St. Louis, Mo.). A Factor Xa cleavage site was also engineered just prior to FLAG to allow removal of this epitope at a later stage. Restriction sites for EcoRI on the 5' end and Not I on the 3' end were also designed into the primers to allow cloning into our expression vector PEAK™ (Edge Biosystems Gaithersburg, Md.). The PCR product was cloned into cloning vector TOPO TA (Invitrogen, Carlsbad, Calif.) and sequenced by using ABI BigDye® Terminator Cycle Sequencing kit (Applied Biosystems, Foster city, CA).

The sequence showed 99% homology with tiger (Panthera tigris) common alpha subunit (Genbank accession number AF354939)

Example 2

Cloning and Sequencing of Feline Thyrotropin β-Subunit

Cloning and sequencing of the fTSH beta "minigene" construct was carried out as follows. The first step was isolation of feline genomic DNA and use of PCR to amplify fTSHβ. QIA Amp® DNA Blood Mini kit (QIAGEN, Valencia, Calif.) was used for isolating feline genomic DNA from white blood cells of two different cats, as per the manufacturer's instructions. Following the experience with human and equine TSH β-subunit, where more expression level of peptide is seen with second intron included than without intron in the sequence, the second intron in beta subunit was retained and the untranslated first exon and first intron were eliminated. Primers were designed using consensus sequences of human, bovine, equine and rat TSHβ, and TSHβ along with the appropriate signal peptide to amplify from genomic DNA as template. Restriction sites for the construct were the same as for the TSHα construct with EcoRI on 5' end and Not I in the 3' end for subsequent cloning into expression vector PEAK™ (Edge Biosystems Gaithersburg, Md.). The PCR products were cloned into TOPO TA (Invitrogen, Carlsbad, Calif.) cloning vector and sequenced.

Example 3

Development of a Yoked Construct with the Human Chorionic Gonadotropin C Terminal Peptide (CTP) Joining the Alpha- and Beta-Subunits The construction of yfTSH was accomplished as follows. The nucleotide sequence encoding the full length alpha subunit excluding the signal sequence was fused in frame with the CTP to the 3' terminus of the β-subunit containing the coding sequence of the signal sequence and the secreted subunit. The α-subunit containing CTP was generated by amplifying the second half of the CTP to the 5' end of the alpha and a restriction cut site, Afl III, was included at the 5' end of the CTP region in the alpha subunit. The first half of the CTP was added to the 3' end of the β-subunit by PCR and the same restriction cut site, Afl III, was included at the 3' end of the CTP region in the β-subunit. The PCR products were cloned into cloning vector TOPO and sequence confirmed. The two pieces were then ligated together by means of T4 DNA ligase and cloned into our expression vector PEAK™ (Edge Biosystems Gaithersburg, Md.). After ligating the two pieces together, the single chain fTSH analog was cloned into TOPO cloning vector and sequence verified.

Example 4

Figure 5A:
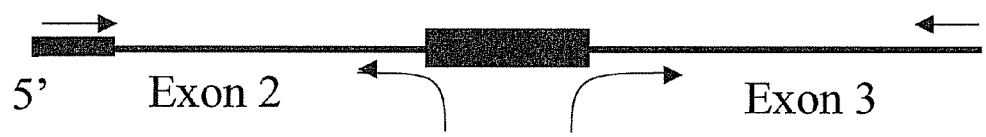
FIGS. 5a and 5b illustrate the strategy used to remove the intron from the thyrotropin β-subunit to prepare the sequence for use in the baculovirus expression system.
Figure 5B:
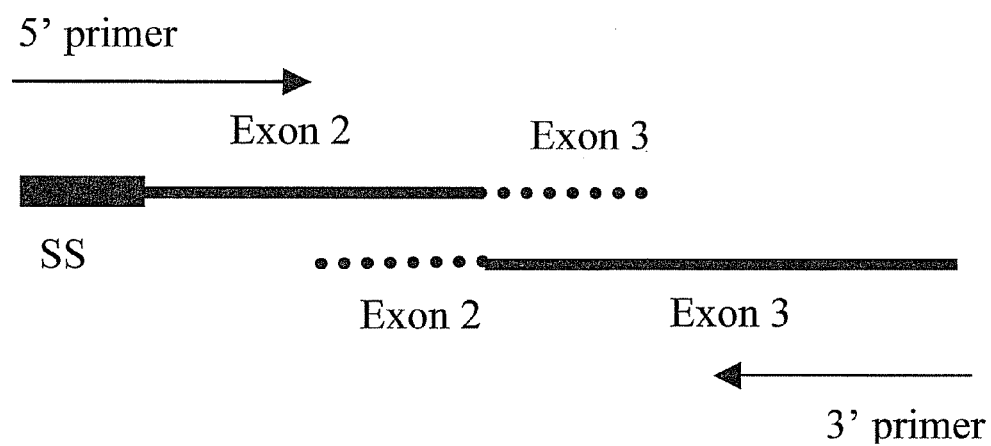

Developing Feline Thyrotropin α-Subunit, Feline Thyrotropin β-Subunit, and Feline Thyrotropin Yoked Constructs for the Baculovirus Expression System Expression System For the first step, overlap PCR was used to remove the intron. Internal primers were designed on either side of the intron and two pieces of TSHβ were amplified separately as shown in FIG. 5a. The two pieces were then overlapped by using both the pieces as templates and a 5' TSHβ-ss primer and a 3' TSHβ-stop primer, as shown in FIG. 5b. The same strategy was followed to remove the intron in the yfTSH except that the 3' primer for the second piece with exon 3 was TSHα-Flag.

PCR was then used to add the Honeybee mellitin (HBM) signal sequence. Since the HBM sequence was too big (63 bp) to add in a single step it was divided into two pieces and then added in a step wise fashion in place of the mammalian signal sequence. Appropriate restriction sites, Eco RI at the 5' and Not I at the 3' end were included for the subsequent cloning into baculovirus transfer vector pvl1393.

The next step was the generation of recombinant baculovirus. BaculoGold transfection Kit was used (Phanningen, San Diego, Calif.) for the generation of recombinant viruses. Baculovirus transfer vector pvl1393 was chosen following our experience with equine TSH, where the same vector showed better expression (70 ng/ml as against 20 ng/ml with other vectors). Pvl1393 has a strong polyhedrin promoter. All the three insect cell constructs were first ligated into the transfer vector using T4 DNA ligase (Fermentas, Hanover, Md.) as per the manufacturers instructions. Sf9 cells (derived from *Spodoptera frugiperda*) were cotransfected with linearized *Baculovirus* DNA provided by the supplier and insect cell construct in pv11393 following manufacturers instructions. Briefly, 0.5 μg of linearized baculovirus DNA and 2.5 μg of the gene of interest in pv11393 was mixed and added onto sf9 cells in transfection solution and incubated for 5 hrs at 27° C. The cells were then washed with fresh media and incubated at 27° C. for 5 days. The viral stock was then amplified 2 rounds and a plaque assay performed to establish the viral titre. Sf9 cells were then infected with recombinant viruses containing TSHα and TSHβ to generate recombinant fTSH α/β heterodimers.

The three insect cell constructs, HBM-fTSHα, HBM-fTSHβ (−), and HBM-yfTSH (−) were cloned into the TOPO TA cloning vector and sequence verified. Recombinant viruses of all three constructs were made and assayed for protein expression by an ELISA developed in our lab (See Example 8).

Example 5

Expression of Feline TSH Constructs (α/β and Yoked) in Three Different Cell Systems The first cell line described is expression of fTSH in the PEAK™ cell line (Modified Human Embryonic Kidney cell). The PEAK stable transfection Kit (Edge Biosystems Gaithersburg, Md.) was used for the transfection of PEAK cells following manufacturer's instructions. In brief, cells were seeded at 30% confluency and 2 hours before transfection, fresh media was added to the flasks. For transfection of a 75 cm² flask, 5 μg of DNA with 125 μl 1.0M CaCl₂ and 500 μl phosphate buffer supplied with the kit were mixed and brought up with sterile water to one ml. The transfection solution was added slowly drop by drop and incubated at 37° C. for 5 hours, then washed with fresh media twice and incubated for 5 days at 37° C. and 5% CO₂.

A stable PEAK™ cell line expressing yfTSH and fTSHα was independently developed using a puromycin selection marker. On third day after transfection, 0.25 μg/ml of puromycin was added to the flask and the dose increased at each passage until a concentration of 2 μg/ml of puromycin was reached. The fTSH α/β heterodimer was expressed by cotransfecting PEAK cells with 5 μg each of fTSH α in PEAK vector and fTSH β in PEAK vector. FTSH α/β, fTSHα and yfTSH were expressed in PEAK cells in quantities between 0.5-2 µg/ml, based upon quantification by ELISA (See Example 8).

Expression of fTSH was also carried out in Sf9 cells. See Example 4 for details on the baculovirus vector system. Co-transfection of Sf9 cells was done as described above for generation of recombinant viruses. The same recombinant baculoviruses described above were used to infect MIMIC™ cells (Invitrogen, Carlsbad, Calif.) that have been engineered to express the mammalian glucosyltransferases.

Example 6

Purification of Glycoproteins Using FLAG Immunoaffinity

Recombinant proteins were immunopurifed from expression media using ANTI-FLAG® M2 monoclonal antibody affinity gel (Sigma Chemical Company, St. Louis, Mo.) following manufacturers instructions. In brief, media was percolated through the column with resin and washed with Tris buffered saline pH 7.4 to remove the unbound protein. Elution was carried out either using 0.1 M Glycine pH 3.5 or excess of FLAG peptide at 100 µg/ml. Five 1 ml eluted fractions were collected, dialyzed against 0.03M phosphate buffer, lyophilized with samples saved for protein assay and sandwich ELISA (See Example 8). For protein determination, the Micro BCA Protein Assay kit (Pierce, Rockford, Ill.) was used following manufacturers instructions.

Since PEAK™ vector has a single promoter, a stable cell line will generally not be expressed by cotransfecting fTSHα-PEAK and fTSHβ-PEAK separately. A stable cell line expressing fTSHα subunit was developed and attempts were made to transiently transfect that cell line with fTSHβ-PEAK. This resulted in no hormonal expression and one explanation for this kind of behavior was that the stable construct dominates the expression activity. A series of fTSHα-PEAK and fTSH β-PEAK transient co-transfections were done and media purified. fTSHα subunit was expressed separately and expressed media purified with the original goal of screening for antibodies against the alpha subunit. Another reason for developing fTSH alpha stable cell line was that since the α-subunit is commonly shared by all glycoproteins, co-transfection of alpha with either feline LHβ or feline FSHβ or feline CGβ will generate heterodimeric glycoproteins. A stable cell line expressing yoked fTSH was generated and media expressing the glycoprotein purified with a final goal to evaluate the bioactivity and immunoreactivity of yfTSH.

Example 7

Preparation of Monoclonal Antibodies Against Fetal Thyrotropin Yoked Polypeptide (Prophetic Example)

In order to prepare monoclonal antibody against feline thyrotropin yoked polypeptide, the yoked polypeptide is emulsified in Complete Freund's Adjuvant and the emulsion used to immunize Balb/c mice (about 50-100 µg antigen per mouse given intraperitoneally). Mice are boosted with an emulsion of antigen-Incomplete Freund's Adjuvant twice at about 10 day intervals (about 50-100 µg antigen each, given intraperitoneally). About ten days after the second booster, an antigen-capture ELISA is run to determine the response of the mice to the yoked polypeptide. The ELISA is then performed using feline thyrotropin yoked polypeptide to coat wells of microtiter plates. After overnight incubation, coated plates are washed thoroughly, and nonspecific binding sites are blocked. After incubation, plates are thoroughly washed. The primary antibody, i.e. antibody contained in the sera from the immunized mice, is diluted and added to the microtiter plate wells. Following additional washes, a goat anti-mouse IgG- and IgM-alkaline phosphatase conjugate are added to the wells. After incubation and thorough washing, the substrate for the phosphatase, p-nitrophenyl phosphate, is added to the wells. The plates are then incubated in the dark for about 10-45 minutes. Subsequently, changes in the absorbance of the plate's contents are read at 405 nm with a microplate spectrophotometer as an indication of mouse response to antigen.

Responding mice are given a final booster consisting of about 5-100 µg, preferably 25-50 µg of feline thyrotropin yoked polypeptide, preferably without adjuvant, administered intravenously. Three to five days after final boosting, spleens and sera are harvested from all responding mice, with the sera being retained for use in later screening procedures. Spleen cells can be harvested by perfusion of the spleen with a syringe. Spleen cells are collected, washed, counted and the viability determined via a viability assay. Spleen and SP2/0 myeloma cells (ATCC, Rockville, Md.) are then screened for HAT sensitivity and absence of bacterial contamination. The screening involves exposing the cells to a hypoxanthine, aminopterin, and thymidine selection (HAT) medium in which hybridomas survive but not lymphocytes or myeloma cells). The cells are combined, the suspension pelleted by centrifugation, and the cells fused using polyethylene glycol solution. The "fused" cells are resuspended in HT medium (RPMI supplemented with 20% fetal bovine serum (FBS), 100 units of penicillin per ml, 0.1 mg of streptomycin per ml, 100 µM hypoxanthine, 16 µM thymidine, 50 µM 2-mercaptoethanol and 30% myeloma-conditioned medium) and distributed into the wells of microtiter plates. Following overnight incubation at 37° C. in 5% $CO_2$, HAT selection medium (HT plus 0.4 µM aminopterin) is added to each well and the cells fed according to accepted procedures known in the art. After 10 days, medium from wells containing visible cell growth are screened for specific antibody production by ELISA. Only wells containing hybridomas making antibody with specificity to the antigen should be retained. The ELISA can be performed as described above, except that the primary antibody added is contained in the hybridoma supernatants. Appropriate controls should be included in each step.

This process should generate several hybridomas producing monoclonal antibodies to the feline thyrotropin yoked polypeptide. Hybridoma cells from wells testing positive for the desired antibodies can be cloned by limiting dilution and re-screened for antibody production using ELISA. Cells from positive wells are then subcloned to ensure their monoclonal nature. The most reactive lines will then be expanded in cell culture and samples frozen in 90% FBS-10% dimethylsulfoxide. The resulting monoclonal antibodies are characterized using a commercial isotyping kit (BioRad Isotyping Panel, Oakland, Calif.) and partially purified with ammonium sulfate precipitation followed by dialysis. The monoclonal antibodies may then further purified using protein-A affinity chromatography.

Example 8

Immunological Detection of Feline Thyrotropin Proteins

Detection was first accomplished using Western Blotting. An immunoaffinity tag called FLAG is added to 3' end of common alpha subunit to help in purification and immunodetection. Anti-FLAG monoclonal antibodies were used for the detection of fTSH heterodimer, yfTSH and fTSHα in Western blotting. fTSH β cannot be detected by this method because it was not engineered to include the FLAG peptide. Briefly, expressed purified protein was loaded onto an SDS PAGE denaturing gel, transferred onto a PVDF/Nitrocellulose membrane, blocked with nonfat dry milk and incubated with Anti-FLAG M2™ monoclonal antibody at 5 µg/ml overnight at 4° C. The membrane was then washed with PBS pH 7.2, incubated with Goat Anti Mouse-HRP (Sigma) at 1:3000 dilution for 1 hour and washed with PBS pH 8.1. The membrane was then incubated with West Dura Super Signal substrate (Pierce, Rockford, Ill.) for 2 minutes and the band imaged and pixel density quantified with a Fluor-S Max MultiImager (Bio-Rad Laboratories, Inc. Hercules, Calif.).

An ELISA for purified protein was also performed. A series of five monoclonal antibodies namely 14H9, 14D8, 15H1, 17A1, 17F6 and a polyclonal antibody were previously generated against pituitary source purified canine TSH (Scripps Laboratories, San Diego, Calif.), Mouse IgG (Cat #1-8765, Sigma Chemical Company, St. Louis, Mo.), Canine TSH (Scripps Laboratories, San Diego, Calif.), Immulon 4HBX strips (ThermoLabsystems, Franklin, Mass.), Goat anti Rabbit and Tetramethyl-benzidine (Sigma Chemical Company, St. Louis, Mo.) were used as standards or reagents.

Immulon 4HBX strips (ThermoLabsystems, Franklin, Mass.) were coated with 14H9 mAb at a rate of 1.5 µg/ml for 12-16 hrs at 4° C., and used as solid phase antibody where as pAb is used in the liquid phase at a rate of 100 ng/100 µl/well. With a mAb on the solid phase, pAb was preadsorbed with mouse IgG (Cat #1-8765, Sigma Chemical Company, St. Louis, Mo.) to block the epitopes which may interact with mAb. Canine TSH (Scripps Laboratories, San Diego, Calif.) was used for generating standard curve and the sensitivity of the assay ranged from 0.31 ng/ml to 20 ng/ml. The mAb-cTSH-pAb antibody complexes were detected using horseradish peroxidase-conjugated Goat anti Rabbit and tetramethyl-benzidine-based chromogenic substance according to the manufacturer's instructions (Sigma Chemical Company, St. Louis, Mo.).

Biotinylation of the pAb and detection using Streptavidin-Aequorin (CHEMICON International, Inc. Temecula, Calif.) or Anti-biotin Aequorin (CHEMICON International, Inc. Temecula, Calif.) as tertiary antibody provided better sensitivity (0.005-0.01 µU/ml) than the colorimetric assay (0.1 µU/ml) where, Aequorin triggered with calcium emits light which can be measured as relative light units (Berthold Technologies, Oak Ridge, Tenn.).

The antibody 14H9 in solid phase and pAb in liquid phase captured fTSH heterodimer and also yfTSH. 17A1 and 17F6 mAbs also detected yfTSH where as 15H1 and 14D8 did not detect yfTSH. This two antibody sandwich assay is routinely used for the monitoring of fTSH expression and purification.

Epitope competition studies using the sandwich combinations of all the five mAbs were done. Twenty five combinations were studied to look at the best monoclonal Ab pair that can capture fTSH. The assays were performed as per the protocol mentioned above.

Some of the mAb combinations like 14H9 on solid phase and all the other four mAbs in the liquid phase, 17A1 in solid phase and 14D8, 15H1 in liquid phase, 17F6 in solid phase, 14D8, 15H1 in liquid phase, 15H1 in solid phase and 14D8 in liquid phase gave a significant signal with canine TSH. All the mAbs except for 14D8 gave a significant signal when paired with pAb. None of the monoclonal antibody sandwiches captured either the fTSH heterodimer or yfTSH. The only antibody pair that identified fTSH was 14H9 and pAb.

Example 9

Biological Activity of Feline TSH Constructs Expressed in Insect and Mammalian Cells A cAMP assay was conducted using the following materials: CHO cells stably transfected with hTSHR (JP09 cells), cAMP salt, Anti-cAMP pAb, 3-isobutyl-1-methylxanthine (IBMX) (all from Sigma Chemical Company, St. Louis, Mo.), Forskolin (Fisher Scientific, Pittsburg, Pa.), I125 to iodinate cAMP (in methyl ester form), 12-well plates.

JP09 cells were grown to confluency in 12 well plates in HF-12 media. The JP09 cells were always kept on Geneticin (Sigma, Chemical Co, St. Louis, Mo.) selection at a rate of 400 µg/ml since being derived as stable hTSHR transfectants. The media was then removed from the plates, cells were washed with sterile PBS and the confluent wells were incubated with serial dilutions of TSH in modified Krebs ringer buffer supplemented with 200 mM sucrose to maintain isotonicity and 1 mM IBMX, for thirty minutes. The buffer was then collected and stored at −80° C. Amount of cAMP released into medium was assayed by radioimmunoassay (RIA) (24). In brief, standards were made using cAMP salt ranging from 50 pmol/ml to 0.1 pmol/ml and unknowns were diluted at 1:25 for TSH and forskolin stimulated wells and 1:10 for basal conditions in 50 mM sodium acetate buffer. For the RIA, 100 µl of standard or sample were succinylated using acetylating reagent (2:1 of tri ethylamine and acetic anhydride) at 2.5 ul/tube and incubated for 4 hrs before adding tracer at 4° C. After adding the tracer at 10000 cpm/tube of I125-cAMP, tubes were incubated overnight at 4° C., then 100 µl of 10% BSA and 2 ml of ethanol were added to tubes, the tubes were spun at 2000×g for 15 min., supernatant was aspirated, and then the tubes were counted in a gamma counter.

Figure 6A:
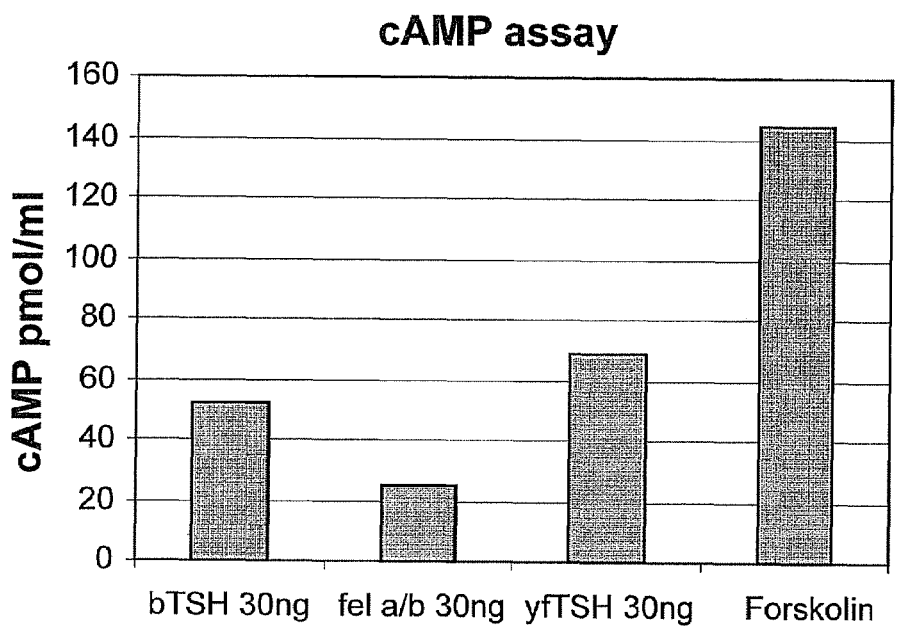
FIGS. 6a and 6b graphically portray the results of a cAMP assay and binding assay (respectively) to demonstrate the efficacy of feline thyrotropin constructs in insect and mammalian cells.

Both fTSH α/β heterodimer and yfTSH were biologically active in terms of cAMP production. fTSH heterodimer at 100 ng concentration produced 25 pmol/ml of cAMP where as yfTSH at the same concentration produced 70 pmol/ml. See the results presented in FIG. 6a.

A binding assay was also conducted using the following materials: $I^{125}$ labelled bTSH, Hanks Balanced Salt Solution, JP09 cells, 12 well plates. 10 µg of bTSH (Obtained from National Hormone and Peptide program, Torrance, Calif.) was iodinated with 0.5 mCi of $I^{125}$. The specific activity was 44 µCi/µg protein. See Chard, T., Sykes, A, Clinical Chemistry, V. 25, 973 (1979) for further details on methodology of the binding assay.

JP09 cells were grown in 12-wells plates till confluency, washed cells twice with HBSS, and then incubated with TSH and $I^{125}$ labeled bTSH (100,000 cpm/well).

Figure 6B:
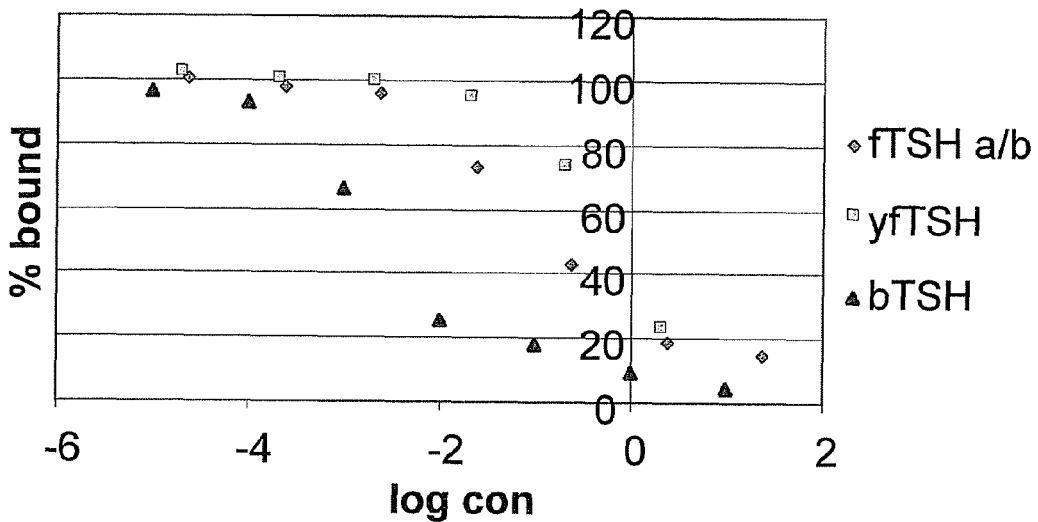

Cells were then washed with HBS and cells solubilized with 1N NaOH. Binding capacity and receptor affinity were then calculated by plotting a scatchard plot using PRISM software. See FIG. 6b. Some preliminary binding studies were done and IC50 values calculated. The reported IC50 value for pituitary source bovine TSH on the human TSH receptor was $3.6 \times 10^{-10}$ M and $B_{max}$ $1.4 \times 10^{-9}$ M. See Nguyen et al., Endocrinology, 143(2), 395 (2002). These results provide evidence for the structural similarity of the recombinant feline TSH to bovine TSH.

The complete disclosures of all patents, patent applications including provisional patent applications, and publications, and electronically available material (e.g., GenBank amino acid and nucleotide sequence submissions) cited herein are incorporated by reference. The foregoing detailed description and examples have been provided for clarity of understanding only. No unnecessary limitations are to be understood therefrom. The invention is not limited to the exact details shown and described; many variations will be apparent to one skilled in the art and are intended to be included within the invention defined by the claims.

```
                          SEQUENCE LISTING

<160> NUMBER OF SEQ ID NOS: 18

<210> SEQ ID NO 1
<211> LENGTH: 118
<212> TYPE: PRT
<213> ORGANISM: Felis sp.

<400> SEQUENCE: 1

Phe Cys Phe Pro Thr Glu Tyr Met Met His Val Glu Arg Lys Glu Cys
 1               5                  10                  15

Ala Tyr Cys Leu Thr Ile Asn Thr Thr Ile Cys Ala Gly Tyr Cys Met
            20                  25                  30

Thr Arg Asp Ile Asn Gly Lys Leu Phe Leu Pro Lys Tyr Ala Leu Ser
        35                  40                  45

Gln Asp Val Cys Thr Tyr Arg Asp Phe Leu Tyr Lys Thr Val Glu Ile
    50                  55                  60

Pro Gly Cys Pro His His Val Thr Pro Tyr Phe Ser Tyr Pro Val Ala
65                  70                  75                  80

Val Ser Cys Lys Cys Gly Lys Cys Asn Thr Asp Tyr Ser Asp Cys Ile
                85                  90                  95

His Glu Ala Ile Lys Thr Asn Asp Cys Thr Lys Pro Gln Lys Ser Asp
            100                 105                 110

Val Val Gly Val Ser Ile
        115

<210> SEQ ID NO 2
<211> LENGTH: 138
<212> TYPE: PRT
<213> ORGANISM: Felis sp.

<400> SEQUENCE: 2

Met Thr Ala Ile Tyr Leu Met Ser Val Leu Phe Gly Leu Ala Cys Gly
 1               5                  10                  15

Gln Ala Met Ser Phe Cys Phe Pro Thr Glu Tyr Met Met His Val Glu
            20                  25                  30

Arg Lys Glu Cys Ala Tyr Cys Leu Thr Ile Asn Thr Thr Ile Cys Ala
        35                  40                  45

Gly Tyr Cys Met Thr Arg Asp Ile Asn Gly Lys Leu Phe Leu Pro Lys
    50                  55                  60

Tyr Ala Leu Ser Gln Asp Val Cys Thr Tyr Arg Asp Phe Leu Tyr Lys
65                  70                  75                  80

Thr Val Glu Ile Pro Gly Cys Pro His His Val Thr Pro Tyr Phe Ser
                85                  90                  95

Tyr Pro Val Ala Val Ser Cys Lys Cys Gly Lys Cys Asn Thr Asp Tyr
            100                 105                 110

Ser Asp Cys Ile His Glu Ala Ile Lys Thr Asn Asp Cys Thr Lys Pro
        115                 120                 125

Gln Lys Ser Asp Val Val Gly Val Ser Ile
    130                 135

<210> SEQ ID NO 3
<211> LENGTH: 96
```

```
<212> TYPE: PRT
<213> ORGANISM: Felis sp.

<400> SEQUENCE: 3

Phe Pro Asp Gly Glu Phe Thr Met Gln Gly Cys Pro Glu Cys Lys Leu
 1               5                  10                  15

Lys Glu Asn Lys Tyr Phe Ser Lys Leu Gly Ala Pro Ile Tyr Gln Cys
                20                  25                  30

Met Gly Cys Cys Phe Ser Arg Ala Tyr Pro Thr Pro Ala Arg Ser Lys
            35                  40                  45

Lys Thr Met Leu Val Pro Lys Asn Ile Thr Ser Glu Ala Thr Cys Cys
        50                  55                  60

Val Ala Lys Ala Phe Thr Lys Ala Thr Val Met Gly Asn Ala Lys Val
 65                 70                  75                  80

Glu Asn His Thr Glu Cys His Cys Ser Thr Cys Tyr His His Lys Ile
                85                  90                  95

<210> SEQ ID NO 4
<211> LENGTH: 120
<212> TYPE: PRT
<213> ORGANISM: Felis sp.

<400> SEQUENCE: 4

Met Asp Tyr Tyr Arg Lys Tyr Ala Ala Val Ile Leu Ala Ile Leu Ser
 1               5                  10                  15

Val Phe Leu His Ile Leu His Ser Phe Pro Asp Gly Glu Phe Thr Met
                20                  25                  30

Gln Gly Cys Pro Glu Cys Lys Leu Lys Glu Asn Lys Tyr Phe Ser Lys
            35                  40                  45

Leu Gly Ala Pro Ile Tyr Gln Cys Met Gly Cys Cys Phe Ser Arg Ala
        50                  55                  60

Tyr Pro Thr Pro Ala Arg Ser Lys Lys Thr Met Leu Val Pro Lys Asn
 65                 70                  75                  80

Ile Thr Ser Glu Ala Thr Cys Cys Val Ala Lys Ala Phe Thr Lys Ala
                85                  90                  95

Thr Val Met Gly Asn Ala Lys Val Glu Asn His Thr Glu Cys His Cys
           100                 105                 110

Ser Thr Cys Tyr His His Lys Ile
           115                 120

<210> SEQ ID NO 5
<211> LENGTH: 244
<212> TYPE: PRT
<213> ORGANISM: Felis sp.

<400> SEQUENCE: 5

Phe Cys Phe Pro Thr Glu Tyr Met Met His Val Glu Arg Lys Glu Cys
 1               5                  10                  15

Ala Tyr Cys Leu Thr Ile Asn Thr Thr Ile Cys Ala Gly Tyr Cys Met
                20                  25                  30

Thr Arg Asp Ile Asn Gly Lys Leu Phe Leu Pro Lys Tyr Ala Leu Ser
            35                  40                  45

Gln Asp Val Cys Thr Tyr Arg Asp Phe Leu Tyr Lys Thr Val Glu Ile
        50                  55                  60

Pro Gly Cys Pro His His Val Thr Pro Tyr Phe Ser Tyr Pro Val Ala
 65                 70                  75                  80

Val Ser Cys Lys Cys Gly Lys Cys Asn Thr Asp Tyr Ser Asp Cys Ile
```

```
                    85                  90                  95
His Glu Ala Ile Lys Thr Asn Asp Cys Thr Lys Pro Gln Lys Ser Asp
            100                 105                 110

Val Val Gly Val Ser Ile Gln Asp Ser Ser Ser Lys Ala Pro Ser
        115                 120                 125

Ala Ser Leu Pro Ser Pro Thr Arg Leu Pro Gly Pro Ser Asp Thr Pro
    130                 135                 140

Ile Leu Pro Gln Phe Pro Asp Gly Glu Phe Thr Met Gln Gly Cys Pro
145                 150                 155                 160

Glu Cys Lys Leu Lys Glu Asn Lys Tyr Phe Ser Lys Leu Gly Ala Pro
                165                 170                 175

Ile Tyr Gln Cys Met Gly Cys Cys Phe Ser Arg Ala Tyr Pro Thr Pro
            180                 185                 190

Ala Arg Ser Lys Lys Thr Met Leu Val Pro Lys Asn Ile Thr Ser Glu
        195                 200                 205

Ala Thr Cys Cys Val Ala Lys Ala Phe Thr Lys Ala Thr Val Met Gly
    210                 215                 220

Asn Ala Lys Val Glu Asn His Thr Glu Cys His Cys Ser Thr Cys Tyr
225                 230                 235                 240

His His Lys Ile

<210> SEQ ID NO 6
<211> LENGTH: 264
<212> TYPE: PRT
<213> ORGANISM: Felis sp.

<400> SEQUENCE: 6

Met Thr Ala Ile Tyr Leu Met Ser Val Leu Phe Gly Leu Ala Cys Gly
1               5                   10                  15

Gln Ala Met Ser Phe Cys Phe Pro Thr Glu Tyr Met Met His Val Glu
            20                  25                  30

Arg Lys Glu Cys Ala Tyr Cys Leu Thr Ile Asn Thr Thr Ile Cys Ala
        35                  40                  45

Gly Tyr Cys Met Thr Arg Asp Ile Asn Gly Lys Leu Phe Leu Pro Lys
    50                  55                  60

Tyr Ala Leu Ser Gln Asp Val Cys Thr Tyr Arg Asp Phe Leu Tyr Lys
65                  70                  75                  80

Thr Val Glu Ile Pro Gly Cys Pro His His Val Thr Pro Tyr Phe Ser
                85                  90                  95

Tyr Pro Val Ala Val Ser Cys Lys Cys Gly Lys Cys Asn Thr Asp Tyr
            100                 105                 110

Ser Asp Cys Ile His Glu Ala Ile Lys Thr Asn Asp Cys Thr Lys Pro
        115                 120                 125

Gln Lys Ser Asp Val Val Gly Val Ser Ile Gln Asp Ser Ser Ser Ser
    130                 135                 140

Lys Ala Pro Ser Ala Ser Leu Pro Ser Pro Thr Arg Leu Pro Gly Pro
145                 150                 155                 160

Ser Asp Thr Pro Ile Leu Pro Gln Phe Pro Asp Gly Glu Phe Thr Met
                165                 170                 175

Gln Gly Cys Pro Glu Cys Lys Leu Lys Glu Asn Lys Tyr Phe Ser Lys
            180                 185                 190

Leu Gly Ala Pro Ile Tyr Gln Cys Met Gly Cys Cys Phe Ser Arg Ala
        195                 200                 205

Tyr Pro Thr Pro Ala Arg Ser Lys Lys Thr Met Leu Val Pro Lys Asn
```

```
                 210                 215                 220
Ile Thr Ser Glu Ala Thr Cys Cys Val Ala Lys Ala Phe Thr Lys Ala
225                 230                 235                 240

Thr Val Met Gly Asn Ala Lys Val Glu Asn His Thr Glu Cys His Cys
                245                 250                 255

Ser Thr Cys Tyr His His Lys Ile
            260

<210> SEQ ID NO 7
<211> LENGTH: 417
<212> TYPE: DNA
<213> ORGANISM: Felis sp.
<220> FEATURE:
<221> NAME/KEY: CDS
<222> LOCATION: (1)..(414)
<223> OTHER INFORMATION: coding region for SEQ ID NO: 2
<220> FEATURE:
<221> NAME/KEY: CDS
<222> LOCATION: (61)..(414)
<223> OTHER INFORMATION: coding region for SEQ ID NO: 1

<400> SEQUENCE: 7 atg act gct atc tac ctg atg tcc gtg ctt ttt ggc ctg gca tgt gga      48
Met Thr Ala Ile Tyr Leu Met Ser Val Leu Phe Gly Leu Ala Cys Gly
 1               5                  10                  15 caa gcg atg tct ttt tgt ttt cca act gag tat atg atg cat gtc gaa      96
Gln Ala Met Ser Phe Cys Phe Pro Thr Glu Tyr Met Met His Val Glu
            20                  25                  30 agg aaa gag tgt gct tat tgc cta acc atc aac acc acc atc tgt gct     144
Arg Lys Glu Cys Ala Tyr Cys Leu Thr Ile Asn Thr Thr Ile Cys Ala
        35                  40                  45 gga tat tgt atg aca cgg gat atc aat ggc aaa ctg ttt ctt ccc aaa     192
Gly Tyr Cys Met Thr Arg Asp Ile Asn Gly Lys Leu Phe Leu Pro Lys
     50                  55                  60 tat gct ctg tcc caa gat gtt tgc acc tac aga gac ttc ctg tac aag     240
Tyr Ala Leu Ser Gln Asp Val Cys Thr Tyr Arg Asp Phe Leu Tyr Lys
 65                  70                  75                  80 act gta gaa ata cca gga tgc cca cac cat gtt act ccc tat ttc tcc     288
Thr Val Glu Ile Pro Gly Cys Pro His His Val Thr Pro Tyr Phe Ser
                 85                  90                  95 tac ccg gta gct gta agc tgt aaa tgt ggc aag tgt aat act gac tat     336
Tyr Pro Val Ala Val Ser Cys Lys Cys Gly Lys Cys Asn Thr Asp Tyr
            100                 105                 110 agc gac tgc ata cat gag gcc atc aag aca aat gat tgt acc aaa ccc     384
Ser Asp Cys Ile His Glu Ala Ile Lys Thr Asn Asp Cys Thr Lys Pro
        115                 120                 125 cag aag tcc gat gtg gta gga gtt tct atc    taa                      417
Gln Lys Ser Asp Val Val Gly Val Ser Ile
    130                 135

<210> SEQ ID NO 8
<211> LENGTH: 835
<212> TYPE: DNA
<213> ORGANISM: Felis sp.

<400> SEQUENCE: 8
atgactgcta tctacctgat gtccgtgctt tttggcctgg catgtggaca agcgatgtct      60 ttttgtttc caactgagta tatgatgcat gtcgaaagga aagagtgtgc ttattgccta     120
accatcaaca ccaccatctg tgctggatat tgtatgacac gggtatgtag ttcatctcac     180
ttcttttagc tgaaaattag ataaacctag actcagtcca tttctatcca gaaaggaaat     240
```

-continued

```
gagataaatc acaacctcat ttcacagacc taacggtcat tggctcctta gaggtagagt    300
ccctaggtta taatatacgg acctactcca tacagttggt acagataatt tttacaatag    360
ttttactccc aaagtttatt taaaccttat cttgttccca cgatcaagga taaaagagag    420
gtgtgtgtgt atgtcatttt tttttgtctc tataggattc agtgtggata tgctgaattg    480
gtattgggga atgggactaa ggaatcctcc cccagtccta tttgtatcta tgggatgtaa    540
gcgaattaac attttgcttc ctcttctgtg cttccctcag gatatcaatg caaactgtt    600 tcttcccaaa tatgctctgt cccaagatgt ttgcacctac agagacttcc tgtacaagac    660
tgtagaaata ccaggatgcc cacaccatgt tactccctat ttctcctacc cggtagctgt    720
aagctgtaaa tgtggcaagt gtaatactga ctatagcgac tgcatacatg aggccatcaa    780
gacaaatgat tgtaccaaac cccagaagtc cgatgtggta ggagtttcta tctaa         835
```

<210> SEQ ID NO 9
<211> LENGTH: 360
<212> TYPE: DNA
<213> ORGANISM: Felis sp.

<400> SEQUENCE: 9

```
atggattact acagaaaata tgcagctgtc attctggcca tactctctgt gtttctgcat     60
attctccatt cttttcctga tggagagttt acaatgcagg ggtgcccaga atgcaagcta    120
aaggaaaaca atacttctc caagttgggt gccccaattt atcaatgcat gggctgctgc    180
ttctccagag catacccccac tccagcaagg tccaagaaga caatgttggt cccaaagaac    240
atcacctcag aagccacatg ctgtgtggcc aaagccttta ccaaggccac ggtaatggga    300
aatgccaaag tggagaatca cacagagtgc cactgcagca cttgctatca ccacaagatt    360
```

<210> SEQ ID NO 10
<211> LENGTH: 459
<212> TYPE: DNA
<213> ORGANISM: Felis sp.
<220> FEATURE:
<221> NAME/KEY: CDS
<222> LOCATION: (100)..(459)
<223> OTHER INFORMATION: coding region for SEQ ID NO: 4
<220> FEATURE:
<221> NAME/KEY: CDS
<222> LOCATION: (172)..(459)
<223> OTHER INFORMATION: coding region for SEQ ID NO: 3

<400> SEQUENCE: 10

```
agttactgag aaatcacaag acgaagccaa atccctctt cagatccacg gtcaactgcc     60
ctgatcacat cctgcaaaaa gtccggagga aggagagcc atg gat tac tac aga        114
                                          Met Asp Tyr Tyr Arg
                                           1               5 aaa tat gca gct gtc att ctg gcc ata ctc tct gtg ttt ctg cat att      162
Lys Tyr Ala Ala Val Ile Leu Ala Ile Leu Ser Val Phe Leu His Ile
            10                  15                  20 ctc cat tct ttt cct gat gga gag ttt aca atg cag ggg tgc cca gaa      210
Leu His Ser Phe Pro Asp Gly Glu Phe Thr Met Gln Gly Cys Pro Glu
        25                  30                  35 tgc aag cta aag gaa aac aaa tac ttc tcc aag ttg ggt gcc cca att      258
Cys Lys Leu Lys Glu Asn Lys Tyr Phe Ser Lys Leu Gly Ala Pro Ile
    40                  45                  50 tat caa tgc atg ggc tgc tgc ttc tcc aga gca tac ccc act cca gca      306
Tyr Gln Cys Met Gly Cys Cys Phe Ser Arg Ala Tyr Pro Thr Pro Ala
55                  60                  65 agg tcc aag aag aca atg ttg gtc cca aag aac atc acc tca gaa gcc      354
```

| | | |
|---|---|---|
| Arg Ser Lys Lys Thr Met Leu Val Pro Lys Asn Ile Thr Ser Glu Ala<br>70                 75                80                85 | | |
| aca tgc tgt gtg gcc aaa gcc ttt acc aag gcc acg gta atg gga aat<br>Thr Cys Cys Val Ala Lys Ala Phe Thr Lys Ala Thr Val Met Gly Asn<br>                  90                    95                   100 | 402 | |
| gcc aaa gtg gag aat cac aca gag tgc cac tgc agc act tgc tat cac<br>Ala Lys Val Glu Asn His Thr Glu Cys His Cys Ser Thr Cys Tyr His<br>             105                  110                115 | 450 | |
| cac aag att<br>His Lys Ile<br>         120 | 459 | |

```
<210> SEQ ID NO 11
<211> LENGTH: 792
<212> TYPE: DNA
<213> ORGANISM: Felis sp.
<220> FEATURE:
<221> NAME/KEY: CDS
<222> LOCATION: (1)..(792)
<223> OTHER INFORMATION: coding region for SEQ ID NO: 6
<220> FEATURE:
<221> NAME/KEY: CDS
<222> LOCATION: (61)..(792)
<223> OTHER INFORMATION: coding region for SEQ ID NO: 5

<400> SEQUENCE: 11
```

| | |
|---|---|
| atg act gct atc tac ctg atg tcc gtg ctt ttt ggc ctg gca tgt gga<br>Met Thr Ala Ile Tyr Leu Met Ser Val Leu Phe Gly Leu Ala Cys Gly<br> 1                 5                  10                 15 | 48 |
| caa gcg atg tct ttt tgt ttt cca act gag tat atg atg cat gtc gaa<br>Gln Ala Met Ser Phe Cys Phe Pro Thr Glu Tyr Met Met His Val Glu<br>             20                  25                 30 | 96 |
| agg aaa gag tgt gct tat tgc cta acc atc aac acc acc atc tgt gct<br>Arg Lys Glu Cys Ala Tyr Cys Leu Thr Ile Asn Thr Thr Ile Cys Ala<br>         35                  40                 45 | 144 |
| gga tat tgt atg aca cgg gat atc aat ggc aaa ctg ttt ctt ccc aaa<br>Gly Tyr Cys Met Thr Arg Asp Ile Asn Gly Lys Leu Phe Leu Pro Lys<br> 50                    55                   60 | 192 |
| tat gct ctg tcc caa gat gtt tgc acc tac aga gac ttc ctg tac aag<br>Tyr Ala Leu Ser Gln Asp Val Cys Thr Tyr Arg Asp Phe Leu Tyr Lys<br>65                 70                75               80 | 240 |
| act gta gaa ata cca gga tgc cca cac cat gtt act ccc tat ttc tcc<br>Thr Val Glu Ile Pro Gly Cys Pro His His Val Thr Pro Tyr Phe Ser<br>             85                  90                95 | 288 |
| tac ccg gta gct gta agc tgt aaa tgt ggc aag tgt aat act gac tat<br>Tyr Pro Val Ala Val Ser Cys Lys Cys Gly Lys Cys Asn Thr Asp Tyr<br>         100                105               110 | 336 |
| agc gac tgc ata cat gag gcc atc aag aca aat gat tgt acc aaa ccc<br>Ser Asp Cys Ile His Glu Ala Ile Lys Thr Asn Asp Cys Thr Lys Pro<br>         115                120               125 | 384 |
| cag aag tcc gat gtg gta gga gtt tct atc cag gac tcc tct tcc tca<br>Gln Lys Ser Asp Val Val Gly Val Ser Ile Gln Asp Ser Ser Ser Ser<br>130                   135                140 | 432 |
| aag gcc cct tcc gcc agc ctt cca agc cca acg cgt ctc ccg ggg ccc<br>Lys Ala Pro Ser Ala Ser Leu Pro Ser Pro Thr Arg Leu Pro Gly Pro<br>145                   150                155              160 | 480 |
| tcg gac acc ccg atc ctc cca caa ttt cct gat gga gag ttt aca atg<br>Ser Asp Thr Pro Ile Leu Pro Gln Phe Pro Asp Gly Glu Phe Thr Met<br>         165                170               175 | 528 |
| cag ggg tgc cca gaa tgc aag cta aag gaa aac aaa tac ttc tcc aag<br>Gln Gly Cys Pro Glu Cys Lys Leu Lys Glu Asn Lys Tyr Phe Ser Lys<br>         180                185               190 | 576 |

-continued

| | | | | | | | | | | | | | | | | |
|---|---|---|---|---|---|---|---|---|---|---|---|---|---|---|---|---|
| ttg | ggt | gcc | cca | att | tat | caa | tgc | atg | ggc | tgc | tgc | ttc | tcc | aga | gca | 624 |
| Leu | Gly | Ala | Pro | Ile | Tyr | Gln | Cys | Met | Gly | Cys | Cys | Phe | Ser | Arg | Ala | |
| | | 195 | | | | 200 | | | | 205 | | | | | | |
| tac | ccc | act | cca | gca | agg | tcc | aag | aag | aca | atg | ttg | gtc | cca | aag | aac | 672 |
| Tyr | Pro | Thr | Pro | Ala | Arg | Ser | Lys | Lys | Thr | Met | Leu | Val | Pro | Lys | Asn | |
| | 210 | | | | | 215 | | | | | 220 | | | | | |
| atc | acc | tca | gaa | gcc | aca | tgc | tgt | gtg | gcc | aaa | gcc | ttt | acc | aag | gcc | 720 |
| Ile | Thr | Ser | Glu | Ala | Thr | Cys | Cys | Val | Ala | Lys | Ala | Phe | Thr | Lys | Ala | |
| 225 | | | | | 230 | | | | | 235 | | | | | 240 | |
| acg | gta | atg | gga | aat | gcc | aaa | gtg | gag | aat | cac | aca | gag | tgc | cac | tgc | 768 |
| Thr | Val | Met | Gly | Asn | Ala | Lys | Val | Glu | Asn | His | Thr | Glu | Cys | His | Cys | |
| | | | | 245 | | | | | 250 | | | | | 255 | | |
| agc | act | tgc | tat | cac | cac | aag | att | | | | | | | | | 792 |
| Ser | Thr | Cys | Tyr | His | His | Lys | Ile | | | | | | | | | |
| | | | 260 | | | | | | | | | | | | | |

<210> SEQ ID NO 12
<211> LENGTH: 1210
<212> TYPE: DNA
<213> ORGANISM: Felis sp.

<400> SEQUENCE: 12

| | | | | |
|---|---|---|---|---|
| atgactgcta | tctacctgat | gtccgtgctt | tttggcctgg | catgtggaca agcgatgtct | 60 |
| ttttgttttc | caactgagta | tatgatgcat | gtcgaaagga | aagagtgtgc ttattgccta | 120 |
| accatcaaca | ccaccatctg | tgctggatat | tgtatgacac | gggtatgtag ttcatctcac | 180 |
| ttcttttagc | tgaaaattag | ataaacctag | actcagtcca | tttctatcca gaaaggaaat | 240 |
| gagataaatc | acaacctcat | ttcacagacc | taacggtcat | tggctcctta gaggtagagt | 300 |
| ccctaggtta | taatatacgg | acctactcca | tacagttggt | acagataatt tttacaatag | 360 |
| ttttactccc | aaagtttatt | taaaccttat | cttgttccca | cgatcaagga taaagagag | 420 |
| gtgtgtgtgt | atgtcatttt | tttttgtctc | tataggattc | agtgtggata tgctgaattg | 480 |
| gtattgggga | atgggactaa | ggaatcctcc | cccagtccta | tttgtatcta tgggatgtaa | 540 |
| gcgaattaac | atttttgcttc | ctcttctgtg | cttccctcag | gatatcaatg caaactgtt | 600 |
| tcttcccaaa | tatgctctgt | cccaagatgt | ttgcacctac | agagacttcc tgtacaagac | 660 |
| tgtagaaata | ccaggatgcc | cacaccatgt | tactccctat | ttctcctacc cggtagctgt | 720 |
| aagctgtaaa | tgtggcaagt | gtaatactga | ctatagcgac | tgcatacatg aggccatcaa | 780 |
| gacaaatgat | tgtaccaaac | cccagaagtc | cgatgtggta | ggagtttcta tccaggactc | 840 |
| ctcttcctca | aaggcccctt | ccgccagcct | tccaagccca | acgcgtctcc cggggccctc | 900 |
| ggacaccccg | atcctcccac | aatttcctga | tggagagttt | acaatgcagg ggtgcccaga | 960 |
| atgcaagcta | aaggaaaaca | aatacttctc | caagttgggt | gccccaattt atcaatgcat | 1020 |
| gggctgctgc | ttctccagag | cataccccac | tccagcaagg | tccaagaaga caatgttggt | 1080 |
| cccaaagaac | atcacctcag | aagccacatg | ctgtgtggcc | aaagccttta ccaaggccac | 1140 |
| ggtaatggga | aatgccaaag | tggagaatca | cacagagtgc | cactgcagca cttgctatca | 1200 |
| ccacaagatt | | | | | 1210 |

<210> SEQ ID NO 13
<211> LENGTH: 130
<212> TYPE: DNA
<213> ORGANISM: Felis sp.

<400> SEQUENCE: 13

| | | | | |
|---|---|---|---|---|
| gtccgatgtg | gtaggagttt | ctatccagga | ctcctcttcc | tcaaaggccc cttccgccag | 60 | ccttccaagc ccaacgcgtc tcccggggcc ctcggacacc ccgatcctcc cacaatttcc    120 tgatggagag                                                           130

<210> SEQ ID NO 14
<211> LENGTH: 851
<212> TYPE: DNA
<213> ORGANISM: Felis sp.

<400> SEQUENCE: 14
gaattcatga ctgctatcta cctgatgtcc gtgcttttttg gcctggcatg tggacaagcg    60
atgtcttttt gttttccaac tgagtatatg atgcatgtcg aaaggaaaga gtgtgcttat   120
tgcctaacca tcaacaccac catctgtgct ggatattgta tgacacgggt atgtagttca   180
tctcacttct tttagctgaa aattagataa acctagactc agtccatttc tatccagaaa   240
ggaaatgaga taaatcacaa cctcatttca cagacctaac ggtcattggc tccttagagg   300
tagagtccct aggttataat atacggacct actccataca gttggtacag ataattttta   360
caatagtttt actcccaaag tttatttaaa ccttatcttg ttcccacgat caaggataaa   420
agagaggtgt gtgtgtatgt catttttttt tgtctctata ggattcagtg tggatatgct   480
gaattggtat tggggaatgg gactaaggaa tcctccccca gtcctatttg tatctatggg   540
atgtaagcga attaacattt tgcttcctct tctgtgcttc cctcaggata tcaatggcaa   600
actgtttctt cccaaatatg ctctgtccca agatgtttgc acctacagag acttcctgta   660
caagactgta gaaataccag gatgcccaca ccatgttact ccctatttct cctacccggt   720
agctgtaagc tgtaaatgtg gcaagtgtaa tactgactat agcgactgca tacatgaggc   780
catcaagaca aatgattgta ccaaaccccca gaagtccgat gtggtaggag tttctatcta   840
agcggccgca t                                                        851

<210> SEQ ID NO 15
<211> LENGTH: 522
<212> TYPE: DNA
<213> ORGANISM: Felis sp.
<220> FEATURE:
<221> NAME/KEY: CDS
<222> LOCATION: (112)..(507)

<400> SEQUENCE: 15
gaattcgccc ttagttactg agaaatcaca agacgaagcc aaaatccctc ttcagatcca    60
cggtcaactg ccctgatcac atcctgcaaa aagtccggag gaaggagagc c atg gat   117
                                                          Met Asp
                                                            1 tac tac aga aaa tat gca gct gtc att ctg gcc ata ctc tct gtg ttt   165
Tyr Tyr Arg Lys Tyr Ala Ala Val Ile Leu Ala Ile Leu Ser Val Phe
        5                   10                  15 ctg cat att ctc cat tct ttt cct gat gga gag ttt aca atg cag ggg   213
Leu His Ile Leu His Ser Phe Pro Asp Gly Glu Phe Thr Met Gln Gly
     20                  25                  30 tgc cca gaa tgc aag cta aag gaa aac aaa tac ttc tcc aag ttg ggt   261
Cys Pro Glu Cys Lys Leu Lys Glu Asn Lys Tyr Phe Ser Lys Leu Gly
 35                  40                  45                  50 gcc cca att tat caa tgc atg ggc tgc tgc ttc tcc aga gca tac ccc   309
Ala Pro Ile Tyr Gln Cys Met Gly Cys Cys Phe Ser Arg Ala Tyr Pro
             55                  60                  65 act cca gca agg tcc aag aag aca atg ttg gtc cca aag aac atc acc   357
Thr Pro Ala Arg Ser Lys Lys Thr Met Leu Val Pro Lys Asn Ile Thr
         70                  75                  80

```
tca gaa gcc aca tgc tgt gtg gcc aaa gcc ttt acc aag gcc acg gta      405
Ser Glu Ala Thr Cys Cys Val Ala Lys Ala Phe Thr Lys Ala Thr Val
        85                  90                  95 atg gga aat gcc aaa gtg gag aat aca gag tgc cac tgc agc act          453
Met Gly Asn Ala Lys Val Glu Asn His Thr Glu Cys His Cys Ser Thr
            100                 105                 110 tgc tat cac cac aag att atc gaa ggt cgt gac tac aag gac gat gac      501
Cys Tyr His His Lys Ile Ile Glu Gly Arg Asp Tyr Lys Asp Asp Asp
115                 120                 125                 130 gat aag taagcggccg ctatg                                             522
Asp Lys <210> SEQ ID NO 16
<211> LENGTH: 132
<212> TYPE: PRT
<213> ORGANISM: Felis sp.

<400> SEQUENCE: 16

Met Asp Tyr Tyr Arg Lys Tyr Ala Ala Val Ile Leu Ala Ile Leu Ser
 1               5                  10                  15

Val Phe Leu His Ile Leu His Ser Phe Pro Asp Gly Glu Phe Thr Met
             20                  25                  30

Gln Gly Cys Pro Glu Cys Lys Leu Lys Glu Asn Lys Tyr Phe Ser Lys
         35                  40                  45

Leu Gly Ala Pro Ile Tyr Gln Cys Met Gly Cys Cys Phe Ser Arg Ala
     50                  55                  60

Tyr Pro Thr Pro Ala Arg Ser Lys Lys Thr Met Leu Val Pro Lys Asn
 65                  70                  75                  80

Ile Thr Ser Glu Ala Thr Cys Cys Val Ala Lys Ala Phe Thr Lys Ala
                 85                  90                  95

Thr Val Met Gly Asn Ala Lys Val Glu Asn His Thr Glu Cys His Cys
            100                 105                 110

Ser Thr Cys Tyr His His Lys Ile Ile Glu Gly Arg Asp Tyr Lys Asp
        115                 120                 125

Asp Asp Asp Lys
        130

<210> SEQ ID NO 17
<211> LENGTH: 1267
<212> TYPE: DNA
<213> ORGANISM: Felis sp.
<220> FEATURE:
<221> NAME/KEY: CDS
<222> LOCATION: (7)..(168)
<220> FEATURE:
<221> NAME/KEY: CDS
<222> LOCATION: (587)..(1252)

<400> SEQUENCE: 17 gaattc atg act gct atc tac ctg atg tcc gtg ctt ttt ggc ctg gca       48
       Met Thr Ala Ile Tyr Leu Met Ser Val Leu Phe Gly Leu Ala
        1               5                  10 tgt gga caa gcg atg tct ttt tgt ttt cca act gag tat atg atg cat      96
Cys Gly Gln Ala Met Ser Phe Cys Phe Pro Thr Glu Tyr Met Met His
 15                  20                  25                  30 gtc gaa agg aaa gag tgt gct tat tgc cta acc atc aac acc acc atc      144
Val Glu Arg Lys Glu Cys Ala Tyr Cys Leu Thr Ile Asn Thr Thr Ile
                 35                  40                  45 tgt gct gga tat tgt atg aca cgg gtatgtagtt catctcactt cttttagctg     198
Cys Ala Gly Tyr Cys Met Thr Arg
```

```
                     50
aaaattagat  aaacctagac  tcagtccatt  tctatccaga  aaggaaatga  gataaatcac    258
aacctcattt  cacagaccta  acggtcattg  gctccttaga  ggtagagtcc  ctaggttata    318
atatacggac  ctactccata  cagttggtac  agataatttt  tacaatagtt  ttactcccaa    378
agtttattta  aaccttatct  tgttcccacg  atcaaggata  aaagagaggt  gtgtgtgtat    438 gtcattttt   tttgtctcta  taggattcag  tgtggatatg  ctgaattggt  attggggaat    498
gggactaagg  aatcctcccc  cagtcctatt  tgtatctatg  ggatgtaagc  gaattaacat    558
tttgcttcct  cttctgtgct  tccctcag gat atc aat ggc aaa ctg ttt ctt           610
                                Asp Ile Asn Gly Lys Leu Phe Leu
                                     55                  60 ccc aaa tat gct ctg tcc caa gat gtt tgc acc tac aga gac ttc ctg            658
Pro Lys Tyr Ala Leu Ser Gln Asp Val Cys Thr Tyr Arg Asp Phe Leu
         65                  70                  75 tac aag act gta gaa ata cca gga tgc cca cac cat gtt act ccc tat            706
Tyr Lys Thr Val Glu Ile Pro Gly Cys Pro His His Val Thr Pro Tyr
     80                  85                  90 ttc tcc tac ccg gta gct gta agc tgt aaa tgt ggc aag tgt aat act            754
Phe Ser Tyr Pro Val Ala Val Ser Cys Lys Cys Gly Lys Cys Asn Thr
95                  100                 105                 110 gac tat agc gac tgc ata cat gag gcc atc aag aca aat gat tgt acc            802
Asp Tyr Ser Asp Cys Ile His Glu Ala Ile Lys Thr Asn Asp Cys Thr
                115                 120                 125 aaa ccc cag aag tcc gat gtg gta gga gtt tct atc cag gac tcc tct            850
Lys Pro Gln Lys Ser Asp Val Val Gly Val Ser Ile Gln Asp Ser Ser
            130                 135                 140 tcc tca aag gcc cct tcc gcc agc ctt cca agc cca acg cgt ctc ccg            898
Ser Ser Lys Ala Pro Ser Ala Ser Leu Pro Ser Pro Thr Arg Leu Pro
        145                 150                 155 ggg ccc tcg gac acc ccg atc ctc cca caa ttt cct gat gga gag ttt            946
Gly Pro Ser Asp Thr Pro Ile Leu Pro Gln Phe Pro Asp Gly Glu Phe
    160                 165                 170 aca atg cag ggg tgc cca gaa tgc aag cta aag gaa aac aaa tac ttc            994
Thr Met Gln Gly Cys Pro Glu Cys Lys Leu Lys Glu Asn Lys Tyr Phe
175                 180                 185                 190 tcc aag ttg ggt gcc cca att tat caa tgc atg ggc tgc tgc ttc tcc           1042
Ser Lys Leu Gly Ala Pro Ile Tyr Gln Cys Met Gly Cys Cys Phe Ser
                195                 200                 205 aga gca tac ccc act cca gca agg tcc aag aag aca atg ttg gtc cca           1090
Arg Ala Tyr Pro Thr Pro Ala Arg Ser Lys Lys Thr Met Leu Val Pro
            210                 215                 220 aag aac atc acc tca gaa gcc aca tgc tgt gtg gcc aaa gcc ttt acc           1138
Lys Asn Ile Thr Ser Glu Ala Thr Cys Cys Val Ala Lys Ala Phe Thr
        225                 230                 235 aag gcc acg gta atg gga aat gcc aaa gtg gag aat cac aca gag tgc           1186
Lys Ala Thr Val Met Gly Asn Ala Lys Val Glu Asn His Thr Glu Cys
    240                 245                 250 cac tgc agc act tgc tat cac cac aag att atc gaa ggt cgt gac tac           1234
His Cys Ser Thr Cys Tyr His His Lys Ile Ile Glu Gly Arg Asp Tyr
255                 260                 265                 270 aag gac gat gac gat aag taagcggccg ctatg                                  1267
Lys Asp Asp Asp Asp Lys
                275

<210> SEQ ID NO 18
<211> LENGTH: 276
<212> TYPE: PRT
<213> ORGANISM: Felis sp.
```

```
<400> SEQUENCE: 18

Met Thr Ala Ile Tyr Leu Met Ser Val Leu Phe Gly Leu Ala Cys Gly
1               5                   10                  15

Gln Ala Met Ser Phe Cys Phe Pro Thr Glu Tyr Met Met His Val Glu
            20                  25                  30

Arg Lys Glu Cys Ala Tyr Cys Leu Thr Ile Asn Thr Thr Ile Cys Ala
        35                  40                  45

Gly Tyr Cys Met Thr Arg Asp Ile Asn Gly Lys Leu Phe Leu Pro Lys
        50                  55                  60

Tyr Ala Leu Ser Gln Asp Val Cys Thr Tyr Arg Asp Phe Leu Tyr Lys
65                  70                  75                  80

Thr Val Glu Ile Pro Gly Cys Pro His His Val Thr Pro Tyr Phe Ser
                85                  90                  95

Tyr Pro Val Ala Val Ser Cys Lys Cys Gly Lys Cys Asn Thr Asp

11. The polypeptide of claim 9 wherein the spacer peptide is the chorionic gonadotropin CTP spacer polypeptide (SEQ ID NO:13).

12. An isolated polynucleotide comprising a nucleic acid sequence encoding the polypeptide of claim 2.

13. The isolated polynucleotide of claim 12, wherein the nucleic acid sequence is selected from the group consisting of SEQ ID NO: 7, SEQ ID NO:8, SEQ ID NO: 11, and SEQ ID NO:12.

14. An isolated feline thyrotropin yoked polypeptide comprising the amino acid sequence SEQ ID NO: 5.

15. A pharmaceutical composition comprising a pharmaceutically acceptable carrier and a polypeptide of claim 2, or a feline thyrotropin yoked polypeptide of claim 14.

16. The pharmaceutical composition of claim 15, wherein the composition is formulated as a single unit dosage.

17. An isolated thyrotropin β-subunit polypeptide comprising an amino acid sequence with at least 99% identity to SEQ ID NO: 1.

18. A kit comprising the thyrotropin β-subunit polypeptide of claim 2 or claim 17 and packaging materials.

19. A kit comprising the thyrotropin β-subunit polypeptide of claim 2 or claim 17 and a radioiodide.

20. A kit comprising the thyrotropin β-subunit polypeptide of claim 2 or claim 17 and an anti-thryotropin antibody.

21. A composition comprising the polypeptide of claim 2 or claim 17.

22. The composition of claim 21 further comprising a mammalian thyrotropin α-subunit polypeptide, wherein said thyrotropin α-subunit polypeptide binds the thyrotropin β-subunit polypeptide and forms a heterodimer that stimulates cells expressing thyroid stimulating hormone receptors (TSH-R) to produce cAMP.

23. The polypeptide of claim 2 or claim 17 linked to an immunogenic carrier.

24. A composition comprising the polypeptide of claim 23.

25. A pharmaceutical composition comprising the isolated polypeptide of claim 17 or the heterodimer of claim 5 or claim 6 and a pharmaceutically acceptable carrier.

26. An immunoassay standard comprising the isolated polypeptide of claim 2 or claim 17.

27. A fusion protein comprising the isolated polypeptide of claim 2 or claim 17.

28. The fusion protein of claim 27, wherein the fusion protein further comprises a mammalian thyrotropin α-subunit polypeptide and wherein said fusion protein stimulates cells expressing thyroid stimulating hormone receptors (TSH-R) to produce cAMP.

29. A method of treating a mammal suspected of having hyperthyroidism, the method comprising:
administering to the mammal a composition comprising the thyrotropin β-subunit polypeptide of claim 2 or claim 17, the yoked polypeptide of claim 14, or the thyrotropin heterodimer of claim 5 or claim 6.

30. The method of claim 29, wherein the mammal is a cat.

31. The method of claim 29, wherein the method further comprises sensitizing the thyroid to increase the response of the thyroid to ablative treatment with radioiodide.

* * * * *